(12) United States Patent
Wang et al.

(10) Patent No.: US 9,708,663 B2
(45) Date of Patent: Jul. 18, 2017

(54) USE OF SAA1B/B HOMOZYGOTE IN THE PROGNOSIS AND DIAGNOSIS OF LIVER CIRRHOSIS

(75) Inventors: Rongfang Wang, Shanghai (CN); Jun Wu, Shanghai (CN); Yan Zhang, Shanghai (CN); Zhenbin Qian, Shanghai (CN)

(73) Assignee: DIASYS DIAGNOSTIC SYSTEMS (SHANGHAI) CO., LTD., Shanghai (CN)

( * ) Notice: Subject to any disclaimer, the term of this patent is extended or adjusted under 35 U.S.C. 154(b) by 397 days.

(21) Appl. No.: 14/364,240

(22) PCT Filed: Mar. 19, 2012

(86) PCT No.: PCT/CN2012/072521
§ 371 (c)(1),
(2), (4) Date: Jun. 10, 2014

(87) PCT Pub. No.: WO2013/086809
PCT Pub. Date: Jun. 20, 2013

(65) Prior Publication Data
US 2015/0031027 A1    Jan. 29, 2015

(30) Foreign Application Priority Data
Dec. 15, 2011    (CN) .......................... 2011 1 0418882

(51) Int. Cl.
| | | |
|---|---|---|
| *C12P 19/34* | (2006.01) | |
| *C12Q 1/68* | (2006.01) | |
| *C07K 14/775* | (2006.01) | |
| *C07K 14/47* | (2006.01) | |
| *C12Q 1/70* | (2006.01) | |

(52) U.S. Cl.
CPC ........ *C12Q 1/6883* (2013.01); *C07K 14/4711* (2013.01); *C07K 14/775* (2013.01); *C12Q 1/6886* (2013.01); *C12Q 1/706* (2013.01); *C12Q 2600/118* (2013.01); *C12Q 2600/156* (2013.01); *G01N 2333/4709* (2013.01); *G01N 2800/085* (2013.01)

(58) Field of Classification Search
USPC .............................................. 435/6.12, 91.2
See application file for complete search history.

(56) References Cited

U.S. PATENT DOCUMENTS

2006/0188902 A1* 8/2006 Narayanan ........... C12Q 1/6816
    435/6.1
2009/0311754 A1* 12/2009 Seitz ................... C12Q 1/6809
    435/91.2

OTHER PUBLICATIONS

Utku et al., Clin. Rheumatol. 26, 927-929 (2007).*
Rychlik et al., Nucleic Acids Research 17(21), 8543-8551 (1989).*

* cited by examiner

*Primary Examiner* — Kenneth Horlick
(74) *Attorney, Agent, or Firm* — Birch, Stewart, Kolasch & Birch, LLP

(57) ABSTRACT

Provided is uses of SAA1β/β(1.5/1.5) homozygote in prognosis and/diagnosis of liver cirrhosis, and in preparation of a reagent for liver cirrhosis prognosis and/or liver cirrhosis diagnosis. Recognition of liver cirrhosis susceptible populations can be achieved by detection of human SAA1β/β homozygote and non-SAA1β/β homozygote through real-time fluorescence quantitative allele specific PCR.

11 Claims, 11 Drawing Sheets

A

B

AA NON-B/B
BB PERCENTAGE
CC HEALTHY CONTROL
DD HEPATITIS B
EE HEPATITIS B LIVER CIRRHOSIS
FF OTHER LIVER CIRRHOSIS

| | | |
|---|---|---|
| Clone 1 | GGGGCTCGGGACATGTGGAGAGCCTACTCTGACATGAGAGAAGCCAATTACATCGGCTCA | 313 |
| | |||||||||||||||||||||||||||||||||||||||||||||||||||||||||||| | |
| α type | GGGGCTCGGGACATGTGGAGAGCCTACTCTGACATGAGAGAAGCCAATTACATCGGCTCA | 373 |
| Clone 1 | GACAAATACTTCCATGCTCGGGGGAACTATGATGCTGCCAAAAGGGGACCTGGGGGTGTC | 373 |
| | ||||||||||||||||||||||||||||||||||||||||||||||||||||||||||  | | |
| α type | GACAAATACTTCCATGCTCGGGGGAACTATGATGCTGCCAAAAGGGGACCTGGGGGTGCC | 433 |
| Clone 1 | TGGGCTGCAGAAGCGATCAG | 393 |
| | |||||||||||||  ||||| | |
| α type | TGGGCTGCAGAAGTGATCAG | 453 |
| Clone 2 | GGGGCTCGGGACATGTGGAGAGCCTACTCTGACATGAGAGAAGCCAATTACATCGGCTCA | 313 |
| | |||||||||||||||||||||||||||||||||||||||||||||||||||||||||||| | |
| β type | GGGGCTCGGGACATGTGGAGAGCCTACTCTGACATGAGAGAAGCCAATTACATCGGCTCA | 373 |
| Clone 2 | GACAAATACTTCCATGCTCGGGGGAACTATGATGCTGCCAAAAGGGGACCTGGGGGTGCC | 373 |
| | |||||||||||||||||||||||||||||||||||||||||||||||||||||||||||| | |
| β type | GACAAATACTTCCATGCTCGGGGGAACTATGATGCTGCCAAAAGGGGACCTGGGGGTGCC | 433 |
| Clone 2 | TGGGCTGCAGAAGTGATCAG | 393 |
| | |||||||||||||||||||| | |
| β type | TGGGCTGCAGAAGTGATCAG | 453 |
| Clone 3 | GGGGCTCGGGACATGTGGAGAGCCTACTCTGACATGAGAGAAGCCAATTACATCGGCTCA | 313 |
| | |||||||||||||||||||||||||||||||||||||||||||||||||||||||||||| | |
| γ type | GGGGCTCGGGACATGTGGAGAGCCTACTCTGACATGAGAGAAGCCAATTACATCGGCTCA | 373 |
| Clone 3 | GACAAATACTTCCATGCTCGGGGGAACTATGATGCTGCCAAAAGGGGACCTGGGGGTGCC | 373 |
| | |||||||||||||||||||||||||||||||||||||||||||||||||||||||||||| | |
| γ type | GACAAATACTTCCATGCTCGGGGGAACTATGATGCTGCCAAAAGGGGACCTGGGGGTGCC | 433 |
| Clone 3 | TGGGCTGCAGAAGCGATCAG | 393 |
| | |||||||||||||  ||||| | |
| γ type | TGGGCTGCAGAAGTGATCAG | 453 |

Fig. 8

USE OF SAA1B/B HOMOZYGOTE IN THE PROGNOSIS AND DIAGNOSIS OF LIVER CIRRHOSIS

TECHNICAL FIELD

The present invention relates to the prognosis of liver cirrhosis and/or diagnosis of liver cirrhosis, and specifically relates to the use of the SAA1β/β homozygote of Serum Amyloid A1 (SAA1) gene as a risk factor of liver cirrhosis in the prognosis of liver cirrhosis and as a biomarker of liver cirrhosis in the diagnosis of liver cirrhosis.

BACKGROUND

Liver cirrhosis is a common clinical chronic liver disease, and is a diffuse lesion damage of liver resulting from one or more prolonged or repeated insults. Liver cirrhosis is a pathologic process of abnormal proliferation of hepatic fibrous-connective tissue when necrosis of liver cells and inflammation occur. Excess hepatic fibrosis causes the atrophy and cirrhosis of liver, which eventually leads to decompensated cirrhosis or hepatic failure and results in patient's death.

Early in 2002, the WHO's statistics showed that nearly 80,000 death cases were caused by liver cirrhosis every year worldwide. Liver cirrhosis has been recognized as one of the ten death leading diseases by 2010. Liver cirrhosis has become a global public health concern because of its high incidence and severity. The most common cause of liver cirrhosis is hepatitis B virus (HBV) or hepatitis C virus (HCV) infection. Approximately one-third of the world population (2,000 million) has been or is being infected by hepatitis B virus, and 350 million of them have suffered the lifelong infection. Moreover, the infectious rate of HBV in China has reached 10% of the whole Chinese population. Consequently, the incidence of liver cirrhosis caused by HBV or HCV infection has been increasing year by year in China. According to an incomplete statistics analysis, there are about 20 million patients with chronic hepatitis B in China, whereas nearly 250,000~300,000 of them may develop into liver cirrhosis, and 50,000~200,000 may develop into liver cancer. Meanwhile, up to 200,000 people die of liver cirrhosis every year in China. Taken together, it would greatly decrease the incidence of liver cirrhosis and liver cancer, thereby reducing the death rate, cutting down the medical expenses and improving the life quality of patients, if the susceptible population could be identified so that early diagnosis and intervention could be applied. It also provides a tool to better understand the pathogenesis of liver cirrhosis and to search for an early intervention protocol, and eventually to better control this complicated disease.

Serum Amyloid A1 (SAA1) is an acute phase reactant protein comprised of 104 amino acids with a molecular weight of about 12-14 kDa under natural conditions. The SAA1 gene is located at chromosome 11 in human beings. SAA1 have been reported by the early researches as an acute phase inflammatory protein because SAA1 can be produced by liver activated macrophages and fibroblasts in an acute inflammation, with the concentration increasing up to 100-1000 folds of the normal value (generally the normal value is 910±270 µL). In addition, SAA1 is an apolipoprotein and can substitute to Apolipoprotien A1 (apoA1) in HDL during the acute phase inflammation thereof regulating cholesterol metabolism. However, recently many researches have shown that SAA1 is not only an acute phase inflammatory protein, but also an opsonin with ininnate immunity. It can interact with proinflammatory cytokines such as IL-6, TNF-α to regulate innate and adaptive immunity. It has been reported that SAA1 played important roles in pathogenesis of developing chronic inflammatory diseases and autoimmune diseases including diabetes, coronary heart diseases and rheumatoid arthritis (RA), etc.

Doctor He et al. in Hong Kong University discovered that SAA1 is significantly increased in the liver of patients suffering from liver cirrhosis and liver cancer. It is known that, after HBV infection, patients can experience three steps: hepatitis, cirrhosis and cancer. Liver cirrhosis develops from the chronic inflammation and/or liver cell necrosis resulting from virus infection and the proliferation of hepatic fibroblasts. It has not been reported yet as to whether SAA1 is directly involved in the aforemetioned pathological changes. Nevertheless, the researches of Pasteur Institute showed that SAA1 is closely interrelated with hepatitis virus infection. In HBV X gene transgenic mouse, the expression of SAA1 was significantly suppressed, indicating that SAA1 may be involved in HBV infection or subsequent pathological changes such as cirrhosis, liver cancer. Therefore, the present invention sets forth that SAA1 is related to the liver cirrhosis caused from hepatitis B, and provides the novel uses of SAA1 in detecting or determining the pathogenesis of liver cirrhosis, diagnosis and interventions.

Gene polymorphism refers to the presence of two or more non-continuous variant genes or genotypes or alleles in one biological species, also called as genetic polymorphism. The Single Nucleotide Polymorphism ("SNP") of genes refers to the variants of a single nucleotide base group in one gene sequence, including the deletion, insertion, and substitution of a single nucleotide group. Human gene polymorphism is involved in the pathogenesis of disease and related to its diagnosis and treatment. Gene polymorphism is vital not only in illustrating the susceptibility and resistance to diseases and toxicants, and various clinical symptoms, but also in predicting the responses and outcomes of medical treatments. Therefore, the study of gene polymorphism has become a hot field in medical sciences.

As distinct racial differences are present in gene polymorphism, different races may reflect big diversities. Therefore, it's important to carry out the studies on the gene polymorphism in relation to liver cirrhosis in the Chinese population as it is vulnerable to the disease. By studying the polymorphism of susceptible genes in liver cirrhosis thereof establishing a detection method, people who carry the susceptible genotypes can be identified. It will be beneficial to the individual targeted therapy of liver cirrhosis. The polymorphism analysis is also important in the outcome prediction of medical treatment of liver cirrhosis patients.

It's known that SAA1 has three alleles: SAA1α, β and γ, and further comprises six genotypes: α/α, α/β, α/γ, β/β, β/γ, and γ/γ (see Table 1). Studies have shown varied proportions of different SAA1 genotypes among the races. In recent years, the correlation between SAA1 genotypes and diseases has been receiving more and more attentions. Many studies have demonstrated that SAA1 genotypes are well associated with some diseases. For example, in the study on SAA1 genotypes of 321 Japanese, Yamade et al. have found that the distribution frequency of allele α (1.1), β (1.5), γ (1.3) among Japanese are 0.310, 0.347 and 0.330 respectively. Ishii et al. have found that the most common genotype for secondary amyloidosis is SAA1γ/γ (1.3/1.3) in 127 RA patients. The occurrence of amyloidosis is highly related to the gene frequency of SAA1γ. In the γ/γ homozygote, the concentration of SAA1 in serum and the ratio of SAA1 to CRP, also an acute phase reactant are higher than those in other genotypes. While among Caucasians, amyloidosis is in direct proportion to the frequency of SAA1α homozygote. In the study of hemorrhagic fever in the Mediterranean, literatures reported that the incidence of SAA1α is seven times higher than the other genotypes. While in the SNP study of SAA1, it is also reported that HDL-C levels of different genotypes varied greatly. Nevertheless, as far as we know, there is no report on the correlation between SAA1 genotypes and liver cirrhosis.

Restriction Fragment Length Polymorphism ("RFLP") is the commonly used method in studying gene polymorphism. This method involves numerous steps and has poor reproducibility, and is not convenient for large-scaled SNP analysis. Therefore, it is important to develop a convenient, fast, accurate and economic SAA1 gene polymorphism detection method for diagnosis of diseases.

By designing SAA1 allele specific reverse primer at which the end of 3'-terminus is located at the SNP site, and is further modified with thiophosphorylation, the present application has developed real-time allele-specific PCR to genotype SAA1. The present invention analyzes SAA1 genotypes and studies the correlation between the SAA1 genotypes and liver cirrhosis. The study results of the present invention show that the distribution of SAA1 genotypes in Chinese population is greatly different from that in the other populations, and the SAA1β/β homozygote do well correlate with the liver cirrhosis, and thereby can be used as a biomarker in the diagnosis and/or prognosis of the liver cirrhosis.

The present invention disclosed for the first time that there exists a positive correlation between SAA1β/β homozygote and hepatitis related liver cirrhosis. The SAA1β/β homozygote, as a biomarker and a high-risk factor of liver cirrhosis, can be used in the diagnosis of liver cirrhosis and the prognosis of hepatitis B patients. Furthermore, the present invention has also evaluated the diagnostic criteria of the SAA1β/β homozygote developing to liver cirrhosis. After a careful screen of the SAA1 homozygote of clinic samples from hepatitis B patients, liver cirrhosis patients, and normal controls with the real-time allele-specific PCR technology reported here, the present invention disclosed for the first time that the significant positive correlation between the SAA1β/β homozygote and liver cirrhosis. The SAA1β/β homozygote is a risk factor of developing liver cirrhosis and is highly valued in the prognosis of liver cirrhosis. Meanwhile, the SAA1β/β homozygote, as a biomarker of liver cirrhosis, has a great significance for developing non-invasive diagnosis reagents for liver cirrhosis. Moreover, the designed primers of the present invention are suitable for detecting human SAA1 SNP with the real-time allele-specific PCR technology. The technology of the present invention can screen liver cirrhosis susceptible individuals in a convenient, accurate and fast manner. The technology is applicable for the study of other SAA1 SNP related diseases.

TABLE 1

SAA1 alleles and their corresponding amino acids

| | amino acid mutation | |
|---|---|---|
| Amino acid site | 52 | 57 |
| SAA1 allele | | |
| α | Val | Ala |
| β | Ala | Val |
| γ | Ala | Ala |

TABLE 1-continued

SAA1 alleles and their corresponding amino acids

| | amino acid mutation | |
|---|---|---|
| Amino acid site | 52 | 57 |
| SAA1 genotype | | |
| β/β | Ala/Ala | Val/Val |
| Non-β/β | | |
| α/α | Val/Val | Ala/Ala |
| α/β | Val/Ala | Ala/Val |
| α/γ | Val/Ala | Ala/Ala |
| β/γ | Ala/Ala | Val/Ala |
| γ/γ | Ala/Ala | Ala/Ala |

SUMMARY OF INVENTION

The present invention provides the identification of SAA1β/β homozygote with the real-time allele-specific PCR technology (the real-time allele-specific PCR) in the diagnosis of liver cirrhosis and/or prognosis of liver cirrhosis The present invention also provides the use of SAA1β/β homozygote in the preparation of prognosis reagent for liver cirrhosis and/or a diagnosis reagent for liver cirrhosis.

In the present invention, four pairs of synthetic primers are constructed according to the gene sequences of the three SAA1α, β and γ alleles, respectively. Samples are amplified by the real-time allele-specific PCR, and the genotypes of the PCR-amplified products are determined to be the SAA1β/β homozygote or non-SAA1β/β homozygote based on CT value and melting curve. When the PCR-amplified product is determined as the SAA1β/β homozygote, the sample is identified as a susceptible individual of liver cirrhosis. By combining the SAA1β/β homozygote with the plasma AST/ALT ratio, TBA and LDL values, the accuracy of non-invasive diagnosis of liver cirrhosis can be greatly improved.

The real-time allele-specific PCR in the present invention refers to a real-time PCR combined with Allele Specific PCR (AS-PCR).

Wherein the primers used in the real-time allele-specific PCR include:

1) a pair of primers of group A3
Forward primer 5'-3' sequence (SEQ ID NO: 1):
TCCCTTCTGCCTTTCCTTTCCTTTCC;

Reverse primer 5'-3' sequence (SEQ ID NO: 2):
TTACGTGATCGCTTCTGCAGCCCAGG 2) a pair of primers of group A2
Forward primer 5'-3' sequence (SEQ ID NO:):
TCCCTTCTGCCTTTCCTTTCCTTTCC Reverse primer 5'-3' sequence (SEQ ID NO: 3):
TTACGTGATCGCTTCTGCAGCCCAGA 3) a pair of primers of group B3
Forward primer 5'-3' sequence (SEQ ID NO: 1):
TCCCTTCTGCCTTTCCTTTCCTTTCC Reverse primer 5'-3' sequence (SEQ ID NO: 4):
TCCCAGGAGCTCCAGTTACGTGATCG -continued

```
4) a pair of primers of group B2
Forward primer 5'-3' sequence (SEQ ID NO: 1):
TCCCTTCTGCCTTTCCTTTCCTTTCC Reverse primer 5'-3' sequence (SEQ ID NO: 5):
TCCCAGGAGCTCCAGTTACGTGATCA
```

Wherein the end of reverse primer 3' terminus is modified by thiophosphorylation.

Wherein the reaction system of the real-time allele-specific PCR comprises the primers, human genomic DNA samples, a pfu DNA polymerase (*Pyrococcus furiosus* DNA polymerase), a reaction buffer and a fluorescent dye.

Wherein, in the real-time allele-specific PCR, plasmids containing cloned genomic DNA fragments of the SAA1α, β, γ alleles, respectively are used as the positive controls, and an empty plasmid as the negative control.

The present invention also provides the use of the SAA1β/β homozygote as a risk factor in the prognosis of liver cirrhosis.

The present invention also provides the use of the SAA1β/β homozygote as a biomarker in the diagnosis of liver cirrhosis.

The present invention disclosed for the first time the correlation between SAA1β/β homozygote and liver cirrhosis based on solid experimental evidence. The present invention reveals the clinic application potential of the SAA1β/β homozygote in the prognosis of liver cirrhosis. The present invention proposed use of the SAA1β/β homozygote that defined as a novel biomarker in the prognosis of liver cirrhosis and the diagnosis of liver cirrhosis. The present invention discloses the distribution of SAA1 genotypes in the healthy Chinese Han population. The present invention provides a convenient, fast, and accurate SAA1β/β homozygote determination method and completes the clinical evaluation of the technology. The present invention also provides a solid basis for establishing methodology of the gene polymorphism determination of other proteins. It also provides a tool for the studies of correlation of gene polymorphism with diseases and thereby application in disease diagnosis.

Studies of the present invention showed that the distribution of SAA1α, β, and γ alleles in Chinese Han population was different from that in Japanese, Caucasian and African populations as previously reported. Among Chinese Han population, allele β was the dominant allele with a percentage of 46.6%, wherein the most were heterozygotes; and alleles α and γ has the lower percentage of 27.4% and 26.0% respectively.

The present invention studied the correlation between SAA1 genotypes and liver cirrhosis, and demonstrated their significance in clinical diagnosis. By determining the genotypes of 427 Chinese population as healthy controls and 103 HBV related liver cirrhosis patients, the present invention disclosed for the first time that in SAA1 genotypes, the percentage of the β/β homozygote is 89.32% among hepatitis B liver cirrhosis, which shows a remarkable positive correlation (r=0.135, P=0.005) with HBV related liver cirrhosis, as compared with the percentage of 31.82% in hepatitis B patients. However, in the healthy controls, the percentage of β/β homozygote is only 8.67%, that is, the proportion of β/β homozygote among hepatitis B liver cirrhosis is 10.3 times that among the healthy controls. Moreover, in the analysis of the diagnosis significance of the β/β homozygote monohybrid versus liver cirrhosis, the area under ROC curve reached 0.79 with 89.32% sensitivity and 68.18% specificity; and the area under ROC curve can reach 0.932 with 76.74% sensitivity and 97.01% specificity after combining with plasma AST/ALT ratio, TBA and LDL values. By further logistic regression analysis, it is disclosed that the odds ratio (OR) of SAA1β/β homozygote to the risk of HBV related liver cirrhosis patients was 17.92 (with the 95% confidence interval of 7.96-40.37). Therefore it indicates that the SAA1β/β homozygote is a risk factor of HBV related liver cirrhosis, which is significant for the prognosis and the diagnosis of liver cirrhosis in the hepatitis B population.

As mentioned above, the present invention disclosed for the first time that in Chinese population, the SAA1β/β homozygote is a high-risk factor for hepatitis B developing to liver cirrhosis, and is highly correlated with HBV related liver cirrhosis, indicating the SAA1β/β homozygote is of high clinic significance in the prognosis and diagnosis of HBV related liver cirrhosis.

In the study on SAA1 genotypes, the present invention establishes a convenient, accurate, and fast real-time allele-specific PCR method for deterring human SAA1 SNP, which can be used in the studies on the correlation between SAA1 SNP and diseases.

In the present invention, the synthesis of the corresponding primers is based on DNA sequences around the SNP sites (at the position of 8052: T, C; at the position of 8067: T, C) of human SAA1α, β and γ alleles. SNP sites is designed to be at the end of the 3' terminus of the reverse primer whereas the forward primer is a conservative intron nucleotide sequence of the SAA1 genome DNA. With the optimized PCR system, the genomic DNA extracted from human peripheral blood cells is amplified by the real-time allele-specific PCR, and the SNP determination is based on the CT value and the melting curve analysis.

The optimization process of the real-time allele-specific PCR used in the present invention comprises the application of pfu DNA polymerase, an appropriate primer modification and the optimization of the PCR system.

In view of possible presence of non-specific amplifications and primer dimerizations during the PCR amplification, a pfu DNA polymerase is preferably used in the present invention. The pfuDNA polymerase has a 5' to 3' terminal DNA synthetase activity and a 3' to 5' terminal DNA exonuclease activity, enabling it not only to carry out the synthesis of DNA but also to promptly identify and excise the mismatched nucleotides, which greatly improves the specificity of PCR amplification and in the meantime lowers the generation of primer dimers.

Preferably, the end of primer 3' terminus is modified by thiophosphorylation so as to prevent the degradation of the primer 3' terminuses due to the 3' to 5' terminal DNA exonuclease activity of pfu DNA polymerase, and thereby further improves the specificity of the amplification.

Moreover, the PCR amplification efficiency and the specificity of amplified products are further improved by selecting the more preferable PCR conditions, such as the concentration range of primers (0.5-5 mM), the primer length (20-30 bp), the annealing temperature (60° C.-67° C.), the amplified product length (120-200 bp), and the concentration range of genome DNA to be tested (5-15 ng), etc.

The present invention applies Syber green in the real-time PCR and compares the differences in CT values of four PCR products of genomic DNA samples by using the primers of four groups A3, A2, B3 and B2, respectively, with those of standard plasmids (containing the genomic DNA fragments of human SAA1α, β, γ alleles, respectively), and thereby further improves the reliability and accuracy of the results.

Based on the principle of AS-PCR, that is, primers can not extend at the end of 3' terminus while mismatches occur, SNP site is designed at the end of 3' terminus and further modified by thiophosphorylation in the real-time allele-specific PCR. On top of it, the use of pfu DNA polymerase further improves the PCR amplification specificity. Therefore, the present invention can determine the SNP site to genotype of SAA1α, β, γ alleles in an accurate and fast manner. In addition, the principle of the technology disclosed in the present invention is also applicable on finding of SNP in other genes.

The present invention provides special primers to determine the SNP in human SAA1 genes and on which grounds classifies the SAA1 genotypes by real-time allele-specific PCR technology. By synthesizing the primers of four groups A3, A2, B3 and B2 based on the specific SNP sequences in human SAA1α, β and γ alleles, the present invention uses pfu DNA polymerase in the real-time PCR to analyze the six human SAA1 genotypes: α/α, α/β, α/γ, β/β, β/γ, γ/γ and thereby distinguishes the sample from the SAA1β/β homozygote to the non-SAA1β/β homozygote. The present invention also uses conventional allele specific PCR (AS-PCR) together with restriction fragment length polymorphism (RFLP) that is old fashion applied to determine gene SNP so as to verify the invention technology: the real-time PCR. Reliability and reproducibility of the high throughput real-time allele-specific PCR has been proved by numours experiments. The present invention establishes for the first time the high throughput real-time allele-specific PCR for determining the SAA1 genotype, its distribution in the healthy Chinese population and the patients suffering from hepatitis B or liver cirrhosis. The real-time allele-specific PCR in the present invention has the merits of easy operation, good accuracy and high throughput etc., and thus is suitable for the large-scaled screening of SAA1α, β and γ genotypes for their correlation with the related diseases in clinics.

The present invention analyzes the six human genotypes SAA1α/α, α/β, α/γ, β/β, β/γ, γ/γ using real-time allele-specific PCR, and thereby determines the SAA1 genotype distribution in the healthy Chinese population and the patients with hepatitis B or liver cirrhosis, and further determines the close correlation between the SAA1β/β homozygote and liver cirrhosis.

The present invention screens the SAA1 genotypes of 427 cases from the healthy Chinese Han population by using real-time allele-specific PCR and RFLP, and further compares the results with the reported distribution frequency of SAA1 genotypes in other races, and hereby specifies the SAA1 genotypes distribution in the Chinese Han population. It also demonstrates the practical application value of the high throughput real-time allele-specific PCR of the present invention.

The present invention carries out the screening of SAA1 genotype in 66 cases of hepatitis B patients using the real-time allele-specific PCR.

The present invention carries out the screening of SAA1 genotype in 103 HBV related liver cirrhosis patients using the real-time allele-specific PCR.

The present invention analyzes the distributions of six SAA1 genotypes in 427 cases of healthy Chinese Han population (healthy controls), 66 cases of chronic hepatitis B patients, and 103 HBV related liver cirrhosis patients. It has been found that the incidence of SAA1β/β homozygote is as high as 89.3% in the liver cirrhosis patients, which is about 10 times higher than that in the healthy controls, and about 3 times higher than that in the chronic hepatitis B patients.

The present invention proposes that using the SAA1β/β homozygote as a new biomarker for liver cirrhosis, and by further combining with the plasma AST/ALT ratio, TBA and LDL values, the accuracy of non-invasive diagnosis of liver cirrhosis could be dramatically improved. The determination of SAA1β/β homozygote of the present invention not only can be used in monitoring the incidence of hepatitis B developing to liver cirrhosis, but also can be applied in developing the reagents for the non-invasive diagnosis of liver cirrhosis.

The present invention also provides a novel test using SAA1β/β homozygote as a biomarker for liver cirrhosis, the test reagent, and the kits for diagnosis of the liver cirrhosis.

In consideration of the important roles and significance of SAA1 genotyping for the prevention, screening, prognosis and diagnosis of susceptible population of related diseases, the studies on the SAA1 genotypes of the present invention provide experimental basis for the pathogenesis of HBV related liver cirrhosis involved with SAA1 protein, establish the high throughput real-time allele-specific PCR for identifying the SAA1β/β homozygote for the susceptible population of liver cirrhosis, and for laying foundations for the early diagnosis and prediction of the treatment outcome of liver cirrhosis. Prevention, diagnosis and intervention for the susceptible population to liver cirrhosis can be made at an early stage so as to significantly decrease the incidence of liver cirrhosis and even liver cancer, which is important not only for the patients but also for the whole society regarding to the economy and healthcare.

BRIEF DESCRIPTION OF THE DRAWINGS

FIG. 8: DNA sequence of the positive clones in Example 1.

PREFERRED EMBODIMENT OF THE INVENTION

Figure 1:
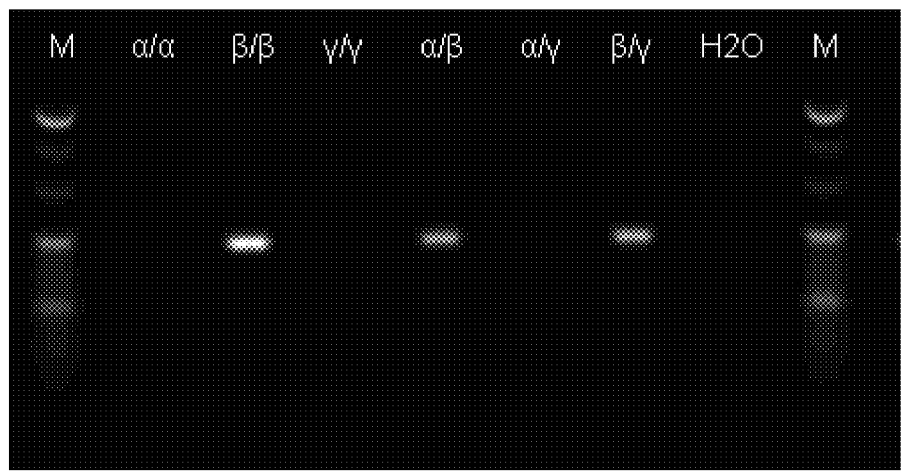
FIG. 1: the schematic diagram of the results of regular AS-PCR. 1A: PCR products analyzed with 3% agarose gel DNA electrophoresis. primers: group B3, the DNA templates: plasmids containing the genomic DNA fragments of human SAA1α, β, γ alleles respectively; 1B: PCR products with or without BanI restriction enzyme cleavage analyzed with 3% agarose gel DNA electrophoresis. primers: group B2, DNA templates: the plasmids containing the genomic DNA fragments of human SAA1α, β, γ alleles respectively.
Figure 1:
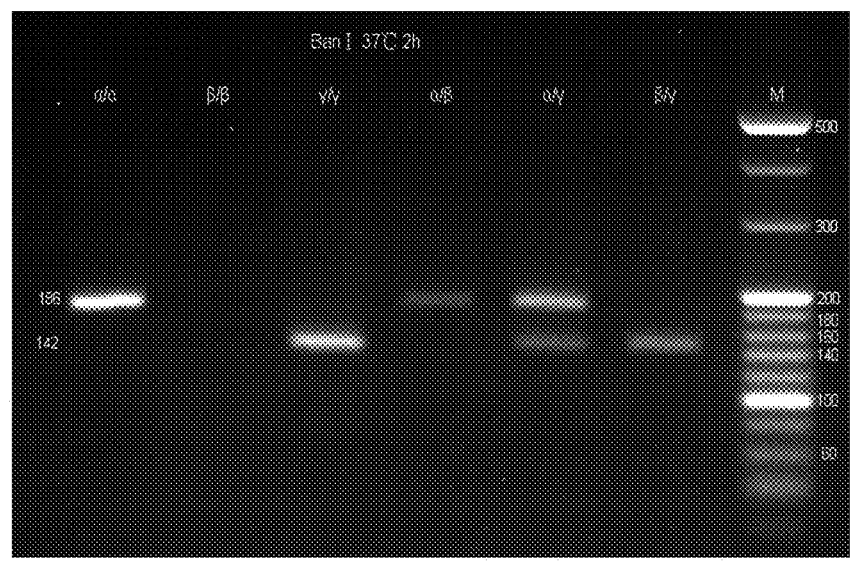

The following examples and drawings are further described in details of the present invention. Based on the principle and scope of the invention, the present invention shall encompass any variation and advantageous that can be understood by common skilled personnels in the field; therefore, the scope of protection shall be complied with the claims annexed hereto.

Example 1

Screening of the SAA1 Genotypes in the Healthy Population

In this example, Allele specific PCR ("AS-PCR") plus Restriction Fragment Length Polymorphism ("RFLP") was used in screening of SAA1 genotypes in the healthy population.

RFLP refers to the difference in fragment lengths of PCR product after digestion of the restriction enzyme among genotypes; such a difference results from the insertion, deletion, rearrangement or point mutation of nucleotide bases at restriction enzyme cleavage sites. RFLP can be used to locate and/or separate specific genes from electrophoretic pattern after enzyme cleavage. This method can be used for determining the difference at the molecular level among species. Of course, it can be used for the study on gene polymorphism.

This example used AS-PCR combined with RFLP to study SAA1 genotypes in healthy population. By comparing with other races, the SAA1 genotypes in the Chinese population were analyzed, and the reason for high incidence of the diseases such as hepatitis B, liver cirrhosis and liver cancer was provided.

Two groups of primer pair were synthesized respectively according to the differences at the position of 8067 in the nucleotide sequences of the three human SAA1α, β, γ alleles, wherein in the primers of group B2 and the primers of group B3 (the primers of group B2 are directed to T at the position of 8067 in β allele; the primers of group B3 are directed to C at the position of 8067 in α and γ alleles), the nucleotides in the position of 8067 were designed to be at the end of reverse primer 3' terminus. The forward primer was a conservative nucleotide sequence of an intron DNA fragment from the SAA1 genome, which was a common primer for groups B2 and B3. DNA extracted from a human blood sample was amplified by AS-PCR reaction, and the presence of SAA1β allele was determined by the absence of the amplified products of the primers of group B3 (if there existed the amplified product after PCR reaction of the primers of group B3, then it was determined that the DNA was positive for the α and γ alleles; if there was no amplified product after PCR with the primers of group B2, but the amplified product after PCR with the primers of group B3, then it was determined that the genomic DNA sample contained SAA1β/β homozygote). Further, enzyme cleavage identification of restriction endonuclease BanI directed to the position of 8052-C in the allele genomic sequence is applied to determine the presence of the site encoding 8052-C according to the fragment lengths after the enzyme cleavage (α allele has no such enzyme cleavage site), and thereby determine the SAA1 genotypes, as shown in Table 3.

Preferably, the AS-PCR Comprises:

(a) Because of usually the presence of non-specific PCR amplification and the primer dimerization, in the present invention, a pfu DNA polymerase that has a 5' to 3' terminal synthetase activity and a 3' to 5' terminal DNA exonuclease activity was applied for not only carrying out the synthesis of DNA but also excising mismatched nucleotides that greatly improved the specificity of PCR, and in the meantime lowered the generation of dimers.

(b) By modifying the end of the primer 3' terminus by thiophosphorylation, degradation of the primer terminus due to the 3' terminal to 5' terminal DNA exonuclease activity of pfu DNA polymerase is prevented, which can further enhance the specificity of PCR.

(c) By optimizing and selecting the preferred reaction system, such as the concentration range of primer (0.5-5 mM), primer length range (20-30 bp), annealing temperature during reaction (60° C.-67° C.), amplified product length (120-200 bp), DNA template concentration range (5-15 ng), and reaction system etc., the efficiency and the specificity of the PCR are further improved.

This Example utilized the characteristic of the primer unable to extend in the presence of mismatches at the end of 3' terminus during a PCR reaction, the SAA1 alleles' SNP sites to be at the end of 3' terminus of the primers with proper modification for the real time allelic specific PCR—In addition, the use of pfu DNA polymerase and other new technologies further optimize a set of conditions such as primer concentration, annealing temperature, amplified fragment length, template DNA concentration etc. With the DNA agarose gel electrophoresis to measure the presence of the amplified products and fragment lengths after BanI enzyme cleavage, the reliable and accurate results were obtained. The present invention not only can screen accurately the SAA1 genotypes in human genome, but also can be applied to study of other genomic DNA mutations.

I. Method of Experiment

1. Obtaining the samples to be tested: extract the human genomic DNA from human peripheral blood cells, i.e., 500 µL human blood was taken and extracted with blood DNA extraction kits from Qiagen, and measured the OD value at 260 nm to calculate the DNA concentration, which was then diluted into a concentration of 10 ng/µL for use.

2. Designing the AS-PCR primers: two groups of AS-PCR primer were designed respectively by referring to allele sequences of human SAA1α, β and γ reported in GenBank: NCBI Reference Sequence: NG_021330.1. The 3' terminus of the reverse primer is located at the SNP mutation site of 8067 in SAA1 genome. Primers used in this Example: the forward primers were common primers located from positions 7909 to 8092; the reverse primers were two groups of primers targeting at the SNP sites of α, β and γ alleles, respectively. The primers of group B2 and group B3 (the primers of group B2 directed to C in the position of 8067 of α and γ alleles; the primers of group B3 directed to T in the position of 8067 of β allele) as listed in Table 2. The end of primer 3' terminus was meanwhile modified by thiophosphorylation.

common forward primers

|tcccttctgcctttcctttcctttcc|aggggctcgggacatgtggagagcctactctgacatgagagaagccaat tacatcggctcagacaaatacttccatgctcgggggaactatgatgctgccaaaaggggacctgggggtgcctgggctgc agaagC (T) gatcacgtaactggagctcctggga The above illustrated is the human SAA1 genomic sequence for AS-PCR primers. Wherein the framed part was a common forward primer tcccttctgcctttcctttcctttcc (SEQ ID NO: 1), the grey-shaded part were reverse primers of the group B, i.e., B3: TCCCAGGAGCTCCAGTTACGTGATCG (SEQ ID NO: 4); B2: TCCCAGGAGCTCCAGTTACGTGATCA (SEQ ID NO: 5), as listed in Table 2.

TABLE 2

AS-PCR Primers

| Primer | | Sequence 5'-3' (The bolded was SNP site at the end of primer 3' terminal) | Amino acids corresponding to SNP site (The bolded was the SNP site) | length of PCR product (bp) |
|---|---|---|---|---|
| Primers of group B3 | common forward primer reverse primer B3 | TCCCTTCTGCCTTTCCTTTCCTTTCC<br>TCCCAGGAGCTCCAGTTACGTGATCG | Amino acid A57(GCC) | about 186 bp |
| Primers of group B2 | common forward primer reverse primer B2 | TCCCTTCTGCCTTTCCTTTCCTTTCC<br>TCCCAGGAGCTCCAGTTACGTGATCA | Amino acid V57(GTC) | |

As shown in Table 2, sequences of a common forward primer and of the reverse primers of the B2 and the B3 groups were listed. The primers of group B2 were designed targeting at T in the position of 8067 of human SAA1β allele (amino acid was V57, whose nucleotide codes were GTC). The primers of group B3 were designed targeting at C in the position of 8067 of human SAA1α and γ alleles (amino acid was A57 whose nucleotide codes were GCC).

The lengths of PCR products with the primers of groups B3 and B2 were 186 bp.

The corresponding relationship between the constructed primers in the present invention and the genotypes was shown in Table 3.

TABLE 3

Results of the regular AS-PCR detected with RFLP (+: band can be detected with RFLP; −: no band can be detected with RFLP)

| | genotype | PCR product using the primers of the group B2 | PCR product using the primers of the group B3 | The length of PCR product after BanI enzyme cleavage |
|---|---|---|---|---|
| homozygote | α/α | + | − | 186 bp |
| | β/β | − | + | − |
| | γ/γ | + | − | 142 and 44 bp |
| Heterozygote | α/β | + | + | 186 bp |
| | α/γ | + | − | 186 and 142 bp |
| | γ/β | + | + | 142 and 44 bp |

Therefore it was Determined that:

(1) if there were product after PCR using the primers of the group B3, but no product after PCR using the primers of the group B2, a sample was SAA1β/β homozygote;

(2) if there were product after PCR reaction using both primers of the group B2 and B3, and the products using the primers of group B2 were further digested with BanI restriction enzyme. If there was a 186 bp band, a sample was α/β genotype; if there were two 142 and 44 bp bands, a sample to be tested was SAA1γ/β genotype;

(3) if there were product after PCR using the primers of the group B2, but no product after PCR using the primers of the group B3, a product using primers of group B2 was digested with the BanI restriction enzyme. If there was a 186 bp band, a sample to be tested was α/α genotype; if there were two bands of 142 and 44 bp, a sample to be tested was SAA1γ/γ genotype; if there were two bands of 186 and 142 bp, a sample to be tested was SAA1α/γ genotype.

3. Cloning and Sequencing of Genome DNA Fragments of Three Human SAA1α, β, γ Alleles 3.1 Design of Primer: Primers were Designed Based on the Reported Human SAA1 Genomic Sequence (SEQ ID NO: 8) (GenBank: NCBI Reference Sequence: NG_021330.1):

Forward primer sequence started from the position of 7796 is CATGGTATCCAAGGCTGCTATGAT (SEQ ID NO: 6);

Reverse primer sequence started from the position of 8256 is ATGAGGAATCACTCACTCCTACCATC (SEQ ID NO: 7).
Sequences from 7796 to 8256:

atggtatccaaggctgctatgatcacaggctgaaagcttgaagtcagtgg aagatttgtccttcctcattcccctctaaggtgttgttggagtctttatg ttctcctgatgtcccttctgcctttcctttcctttccaggggctcgggac atgtggagagcctactctgacatgagagaagccaattacatcggctcaga caaatacttccatgctcggggga actatgatgctgccaaaagggga cctg ggggtgcctgggctgcagaagtgatcacgtaactggagctcctgggacgt tagggctgggtgagcagagcttgcctgccttggacagtcaggagggagac gagctccttgtggagaagttagaggctgcggcccctcctcctcttgccct ctctctgcctctgtgctcagtgtgaggtctgagtggatggtaggagtgag tgattcctcat 3.2 PCR System:
following reagents were added into a 200 μL microPCR tube:

| 10XPCR buffer | 5 μL; |
|---|---|
| Template genome DNA | 1 μg; |
| dNTP | 1 mM; |
| the forward and the reverse primers, respectively | 100 pM. |
| pfu DNA polymerase | 2 U |
| deionized sterile water to make volume to final 50 μL. | |

PCR cycle conditions: 94° C. for 5 minute, 94° C. for 30 seconds, 54° C. for 1 minute; 72° C. for 1 minute, 40 cycles; then extension at 72° C. for 10 minutes.

3.3 Cloning of PCR product: the PCR product was harvested with a PCR product extraction kit, and end blunted with T4 DNA polymerase. After agarose gel electrophoresis, a targeted product was purified with a gel extraction kit and then inserted into EcoRV site in pBluesecriptII SK(+) plasmid (see Sambrooks, Molecular Cloning Manual). The plasmid was then transformed into *E. coli* DH5α strain, and positive clones were screened with PCR.

3.4 Three positive clones containing SAA1α, β, γ alleles were picked and sequenced. Results were aligned with the sequence in genebank and found to be consistent. The results are shown in FIG. 8. The plasmids containing SAA1α, β, γ alleles respectively were purified from corresponding *E. coli* clones as positive controls in AS-PCR and real time allelic specific PCR.

4. AS-PCR Method:
4.1 Sample of human genome DNA was diluted to 10 ng/μL as a DNA template, and subjected to AS-PCR using the primers of the groups B2 and B3 respectively. The positive controls were the three cloned plasmids described above and empty plasmid as the negative control.

4.2 AS-PCR System was:

| 10X buffer | 2.50 μL |
|---|---|
| gDNA(or plasmid DNA) | 15 ng(0.05 ng) |
| dNTP(25 mM) | 2.5 μL |
| MgSO₄(25 mM) | 2 μL |
| Forward primer (10 uM) | 1 μL |
| Revers primers(B3/B) | 1 μL |

-continued

| pfu DNA polymerase | 0.5 μL |
|---|---|
| H₂O was added to make the final volume become 25 uL. | |

PCR cycle conditions: 95° C. for 5 min; 95° C. for 30 seconds; 62° C. for 30 seconds; 72° C. for 1 minute; 35 cycles.
PCR product was analyzed with 3% agarose gel electrophoresis.

5. RFLP Detection of AS-PCR Product:
PCR product was purified with a gel extraction kit, and then digested with restriction endoclunease BanI at 37° C. for 2 hours. The product was detected and analyzed with the 3% agarose gel electrophoresis.

6. Establishment of Positive Controls
Plasmids containing genome DNA fragments of SAA1α, β and γ alleles were mixed to make 6 combinations, i.e., α/α, α/β, α/γ, β/β, β/γ, γ/γ genotypes as positive DNA templates for AS-PCR followed by RFLP detection. The reaction conditions of AS-PCR were: 95° C. for 5 minutes; 62° C. for 30 seconds; 72° C. for 1 minute; 35 cycles.

Results are shown in FIG. 1.1A: result of AS-PCR using the primers of the group B3; 1B: result of AS-PCR using the primers of the group B2. The PCR product was digested with BanI enzyme.

Plasmids containing genome DNA fragments of SAA1α, β and γ alleles were tested with AS-PCR detected by RFLP. Results point-to-point agreed to the primers corresponding with the genotypes as listed in Table 3, which demonstrated that the positive controls met the experimental requirements.

II. Result Analysis
1. Distribution of SAA1 Genotypes in Chinese Han Population (See Table 4)

The distribution of SAA1 genotypes in Chinese Han population detected in the present invention is shown in Table 4. In the Chinese Han population, the percentage of α/β genotype was the highest as 41.22%; followed by β/γ genotype with 34.67%; β/β homozygote as 8.67%; γ/γ homozygote as 3.98%; and the percentage of α/α homozygote was the lowest, which was 2.11%.

2. Comparison of Distribution Frequency of SAA1 Genotypes in Chinese Population with that in Other Races (See Table 5)

Distribution frequency of SAA1 alleles in Chinese Han population was analyzed and compared with the reported distribution frequencies in Caucasian and Japanese. As shown in Table 5, in Chinese Han population, SAA1β allele had the highest frequency as 46.6%, which was 2.5 times that in Caucasian (18.9%), and was also higher than that in Japanese (30.1%). However the frequency of SAA1α allele was 27.4%, which was much lower than that in Caucasians (75.8%), and also lower than that in Japanese (32.5%). The frequency of SAA1γ allele was 26%, which was intermediate between that in Caucasians (5.3%) and that in Japanese (37.4%). Studies have shown that in Japanese RA patients, the most common genotypes was γ/γ homozygote for the incidence of AA-type amyloidosis, while the frequency of Mediterranean fever in Caucasian was positively correlated to the frequency of SAA1α. Furthermore, incidence of hepatitis B and HBV related liver cirrhosis in Chinese was much higher than those in Caucasian and in Japanese. Studies also reported that the content of SAA1 protein increased dramatically in the plasma of liver cancer patients. Therefore, it has been indicated that SAA1 alleles polymorphism could be related to the high incidence of hepatitis B, liver cirrhosis, and liver cancer in Chinese.

TABLE 4

Distribution of SAA1 genotypes in Chinese Han population

| SAA1 genotype | cases | percentage (%) |
|---|---|---|
| α/α | 9 | 2.11 |
| α/β | 176 | 41.22 |
| α/γ | 40 | 9.37 |
| β/β | 37 | 8.67 |
| β/γ | 148 | 34.67 |
| γ/γ | 17 | 3.98 |

TABLE 5

Distribution of SAA1 alleles in Chinese, Caucasian and Japanese

| allele | Chinese | Caucasian [a] frequency (%) | Japanese [b] |
|---|---|---|---|
| α | 27.4 | 75.8 | 32.5 |
| β | 46.6 | 18.9 | 30.1 |
| γ | 26.0 | 5.3 | 37.4 |
| total | 427 | 95 | 103 |

[a] Amyloid. 1998 Dec; 5(4):262-5.
[b] Hum Genet (1999) 105:360-366

Example 2

Correlation Between Human SAA1β/β Homozygote and HBV Related Liver Cirrhosis and the Use of the Art Through screening and studies on distribution of the SAA1β/β homozygote and the non-SAA1β/β homozygote in hepatitis B patients and HBV related liver cirrhosis patients by using real-time allele-specific PCR, the present invention demonstrated a strong correlation between the SAA1β/β homozygote and HBV related liver cirrhosis, and herewith suggested that SAA1β/β homozygote can be used in the diagnosis/prognosis of liver cirrhosis.

Real-time PCR technology has the characteristics of real-time monitoring, quantitative analysis and high throughput, and can be operated easily with a high sensitivity. SYBR Green I fluorescent dye added in the reaction can emit fluorescence when specifically inserting into the double-stranded DNA molecule. When the DNA molecule is in an denature status (single-strand) at the highest temperature during PCR cycle, the dye is released, and fluorescence is bleached. Therefore in a real-time PCR system, the fluorescence intensity is positively correlated to the content of the double-stranded DNAs. Thus by collecting fluorescence signals in each cycle, the changes of the amount of the DNA product can be monitored via the measurement of fluorescence intensity, and thereby a fluorescence intensity versus PCR cycle curve can be obtained. Eventually, the amount of PCR product of each reaction cycle in the PCR system can be calculated.

The principle of allele specific PCR (AS-PCR) is based on that Taq DNA polymerase cannot repair the mismatch occurring at the end of 3' terminus of a DNA primer to a DNA template. Therefore, when the nucleotide at the end of 3' terminus of a primer is completely matched with the mutation site of an allele DNA that is used as a template in the AS-PCR, an amplification happens; on the other hand, when the nucleotides at the end of 3' terminus mismatch with the template, the template DNA would not be amplified or would have a very low amplification efficiency. Therefore, the SAA1 genotype can be determined by analysis of the AS-PCR product.

The present invention uses the above mentioned AS-PCR further modified to be a real-time allelic specific PCR to real time monitor changes of each cycle during an AS-PCR thereby detecting the SAA1 SNP sites corresponding to the amino acid at sites V57A and V52A in SAA1α, β, and γ alleles. Clinic tests were conducted in 66 hepatitis B patients (have not yet developed to liver cirrhosis) and 103 HBV related liver cirrhosis patients, and a feasibility of these alleles as a biomarker of liver cirrhosis was evaluated.

Based on the nucleotide sequences from the position 7800 to the position 8300 of the complete SAA1 genome (GenBank: NCBI Reference Sequence: NG_021330.1), the present invention detected the three SNP sites in SAA1α, β, γ alleles by using the real-time allele-specific PCR.

Primers were synthesized according to the SNP sequence (GenBank: NCBI Reference Sequence: NG_021330.1) (T or C in the position of 8052; T or C in the position of 8067) of human SAA1α, β, γ alleles, the SNP sites were designed at the end of 3' terminus of the reverse primers, and the forward primer was a conservative nucleotide sequence from SAA1 genome. By the real-time allele-specific PCR, the DNA template extracted from human blood sample can be used for SAA1 genotyping by analyses of $C_T$ values and melting curves.

I. Experiment Method

1. Preparation of samples: human whole blood (500 μL) was treated with a blood DNA extraction kit to extract genome DNA. The DNA concentration was measured at 260 nm and then diluted to make a working concentration at 10 ng/μL.

2. Design of the real-time allele-specific PCR (real-time AS-PCR) primers: four groups of primers, A3, B3, A2 and B2, were based on the reported human SAA1α, β and γ allele sequences. The end of 3' terminus of each reverse primer is at the SAA1 allele SNP site. The primers were designed according to SAA1α, β and γ genomic DNA sequences (GenBank: NCBI Reference Sequence: NG_021330.1). The forward primer was a common primer located at 7907~7933 bp (GenBank: NCBI Reference Sequence: NG_021330.1); with four reverse primers comprised four primer groups: A3, B3, A2 and B2 that matched to the polymorphism sites of α, β and γ alleles, whose ends of the 3' terminus was located at the position of 8052 or the position of 8067 respectively as shown in Table 6. In addition, the ends of the 3' terminus of primers were modified by thiophosphorylation so as to improve the specificity of the real-time AS-PCR common forward primer tcccttctgcctttcctttcctttcc agggctcgggacatgtggagagcctactct gacatgagagaagccaattacatcggctcagacaaatacttccatgctcgggggaactatg -continued

```
atgctgccaaaaggggacctgggggtg|CctgggctgcagaagCgatcacg taa|ctggagc
tcctggga
```

The Primers of Group A the Primers of Group B

The above illustrated is the human SAA1 genomic sequence for the real-time AS-PCR. The first framed part was the common forward primer: tcccftctgcctttcctttcctttcc (SEQ ID NO: 1), the second framed part was two reverse primers of the primers of group A, i.e., A3, A2: CctgggctgcagaagCgatcacg taa; the gray-shaded sequence was for the two reverse primers of the primers of group B, i.e., B3, B2: Cgatcacg taactggagc tcctggga, as shown in Table 6.

TABLE 6

Real-time AS-PCR primers

| Primer | | Sequence (The bolded was SNP site at the end of primer 3' terminus) | Amino acids corresponding to SNP site (The bolded was the SNP site) | Length of PCR product (bp) |
|---|---|---|---|---|
| Primers of group A3 | common forward primer A | TCCCTTCTGCCTTTCCTTTCCTTTCC | A52 (GCC) | About 168 bp |
| | reverse primer A3 | TTACGTGATCGCTTCTGCAGCCCAGG | | |
| Primers of group A2 | common forward primer A | TCCCTTCTGCCTTTCCTTTCCTTTCC | V52 (GTC) | About 168 bp |
| | reverse primer A2 | TTACGTGATCGCTTCTGCAGCCCAGA | | |
| Primers of group B3 | common forward primer B | TCCCTTCTGCCTTTCCTTTCCTTTCC | Amino acid A57 (GCC) | About 184 bp |
| | reverse primer B3 | TCCCAGGAGCTCCAGTTACGTGATCG | | |
| primers of group B2 | common forward primer B | TCCCTTCTGCCTTTCCTTTCCTTTCC | V57 (GTC) | About 184 bp |
| | reverse primer B2 | TCCCAGGAGCTCCAGTTACGTGATCA | | |

In Table 6, the primers A and B are identical as the common forward primer of groups A and B, respectively; the primers A2 and A3 are the reverse primers of the groups A2 and A3, respectively; and the primers B2 and B3 are the reverse primers of the groups B2 and B3, respectively. The primers of the group A2 were designed match to Tat the position of 8052 (amino acid: V52GTC) of human SAA1α allele. The primers of the group A3 were designed match to C at the position of 8052 (amino acid: A52 (GCC)) of human SAA1γ, β alleles. The primers of group B2 were designed match to T at the position of 8067 (amino acid: V57 (GTC)) of human SAA1β allele. The primers of group B3 were designed match to C at the position of 8067 (amino acid: A57 (GCC)) of human SAA1α, γ alleles.

The lengths of the PCR products using the primers of groups A3 and A2 were 168 bp. The lengths of PCR products using the primers of groups B3 and B2 were 184 bp.

The correspondence between the designed primers and SAA1 genotypes was shown in Table 7.

TABLE 7

Results of the real-time AS-PCR

| | genotype | A3 | B3 | A2 | B2 |
|---|---|---|---|---|---|
| homozygote | α/α | − | + | + | − |
| | β/β | + | − | − | + |
| | γ/γ | + | + | − | − |

TABLE 7-continued

Results of the real-time AS-PCR

| | genotype | A3 | B3 | A2 | B2 |
|---|---|---|---|---|---|
| Heterozygote | α/β | +/− | +/− | +/− | +/− |
| | α/γ | +/− | +/+ | +/+ | − |
| | γ/β | +/− | +/− | −− | +/− |

(+: positive for PCR product band; −: negative for PCR product band).

3. Cloning and sequencing of genome DNA fragment of human SAA1α, β, γ alleles: which are the same as that in Example 1.

4. The real-time AS-PCR: human genomic DNA (gDNA, 10 ng/μL) was used as DNA template in the real-time AS-PCR. Positive controls were the plasmids containing the three cloned and sequenced genomic DNA fragments of human SAA1 alleles (α, β, γ), respectively, the negative control was empty plasmid without SAA1 DNA fragments. Reaction system and conditions were listed as follows:

| | |
|---|---|
| 10X buffer | 2 μL |
| gDNA(10 ng) | 15 ng |
| dNTP(40 mM) | 2 mM |
| MgSO$_4$(50 mM) | 7.5 mM |
| Common forward primer (10 uM) | 0.2 μM |
| Reverse primer (A3/B3/A2/B2) | 0.2 μM |
| 20XSYBR (cyanine-containing flourecent dye) (Shanghai Shinegene Molecular Biotechnology Ltd.) | 0.3 μL |
| 50X ROX (flourescent dye) ((Shanghai Shinegene Molecular Biotechnology Ltd.) | 0.05 μL |
| pfu DNA polymerase | 0.5 μL |
| H$_2$O | to the final volume 20 μL |

The real-time AS-PCR Cycle conditions: 95° C. for 5 min; 95° C. for 30 seconds; 62° C. for 31 seconds; 72° C. for 45 seconds; 35 cycles.

Figure 2:
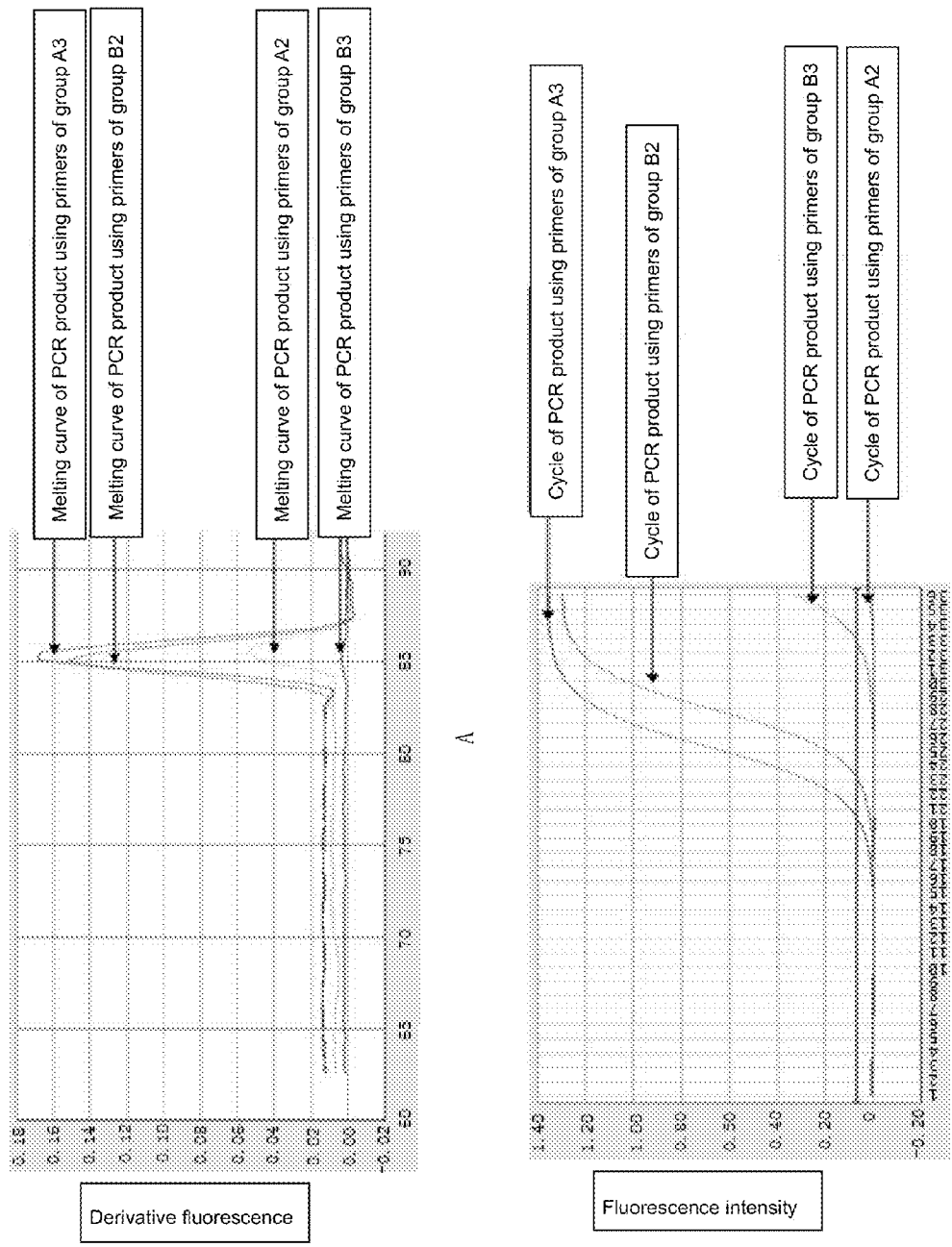
FIG. 2: the schematic diagram of the real-time allele-specific PCR results using a plasmid containing the genomic DNA fragment of the human SAA1β allele as a template. 2A: Melting curve of the real-time allele-specific PCR; 2B: the fluorescence amplification curve of the real-time allele-specific PCR; 2C $C_T$ values of the real-time allele-specific PCR using the different pairs of the primers as indicated on the pictures.
Figure 2:
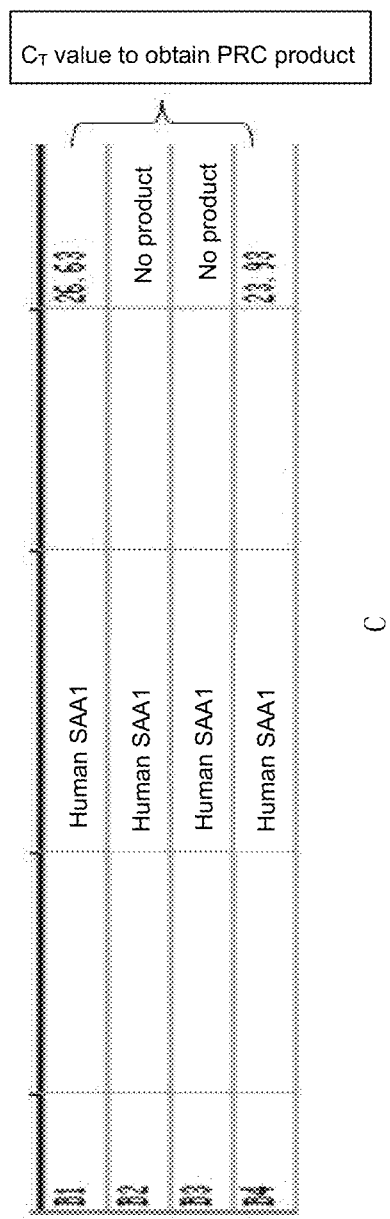
Figure 3:
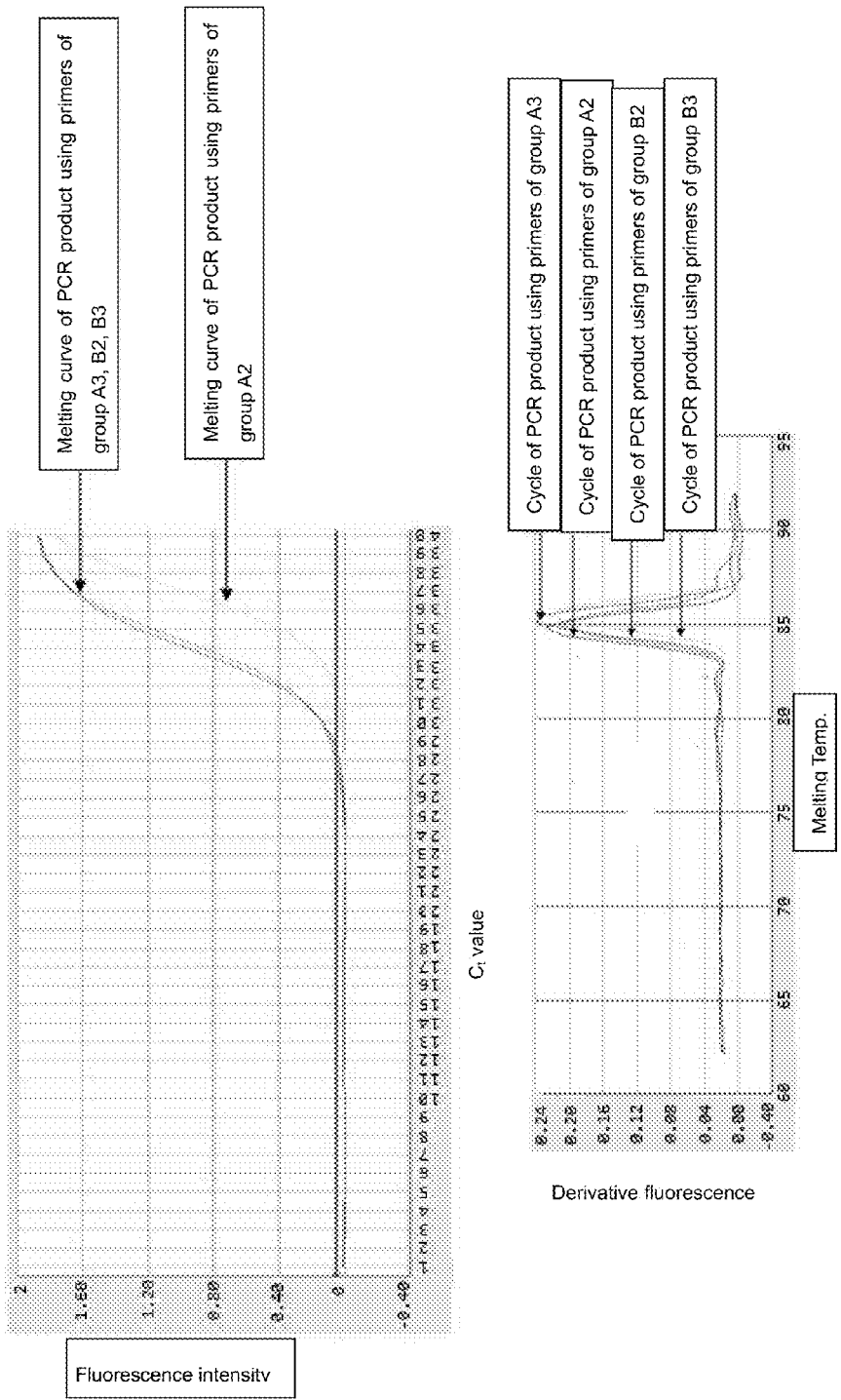
FIG. 3: the schematic diagram of detection result of the human SAA1 genotypes by real-time allele-specific PCR. 3A: Melting and reaction curves of the SAA1α/β genotype; 3B: Melting and reaction curves of the SAA1β/β genotype; 3C: Melting and reaction curves of the SAA1γ/β genotype.
Figure 3:
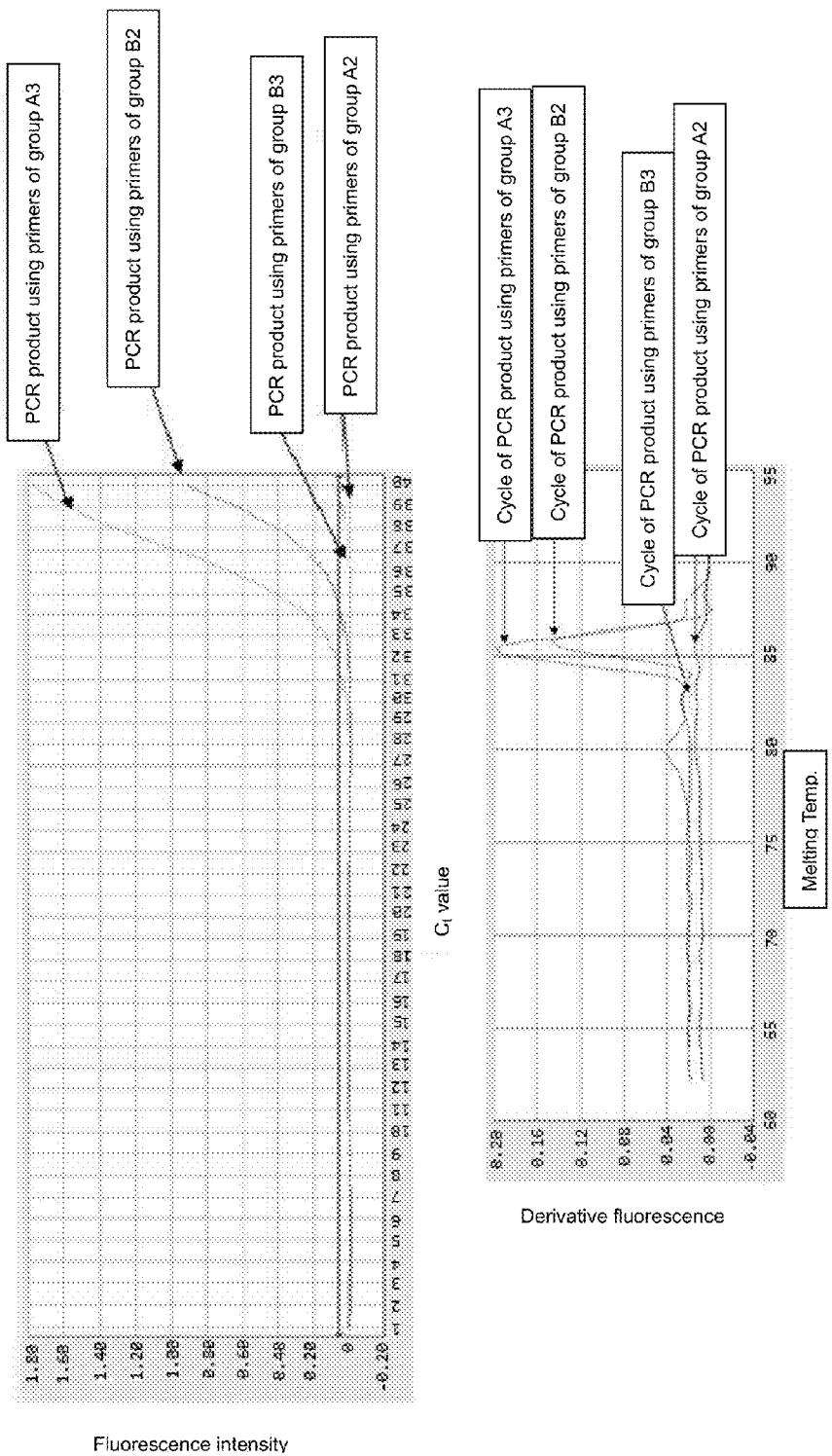
Figure 3:
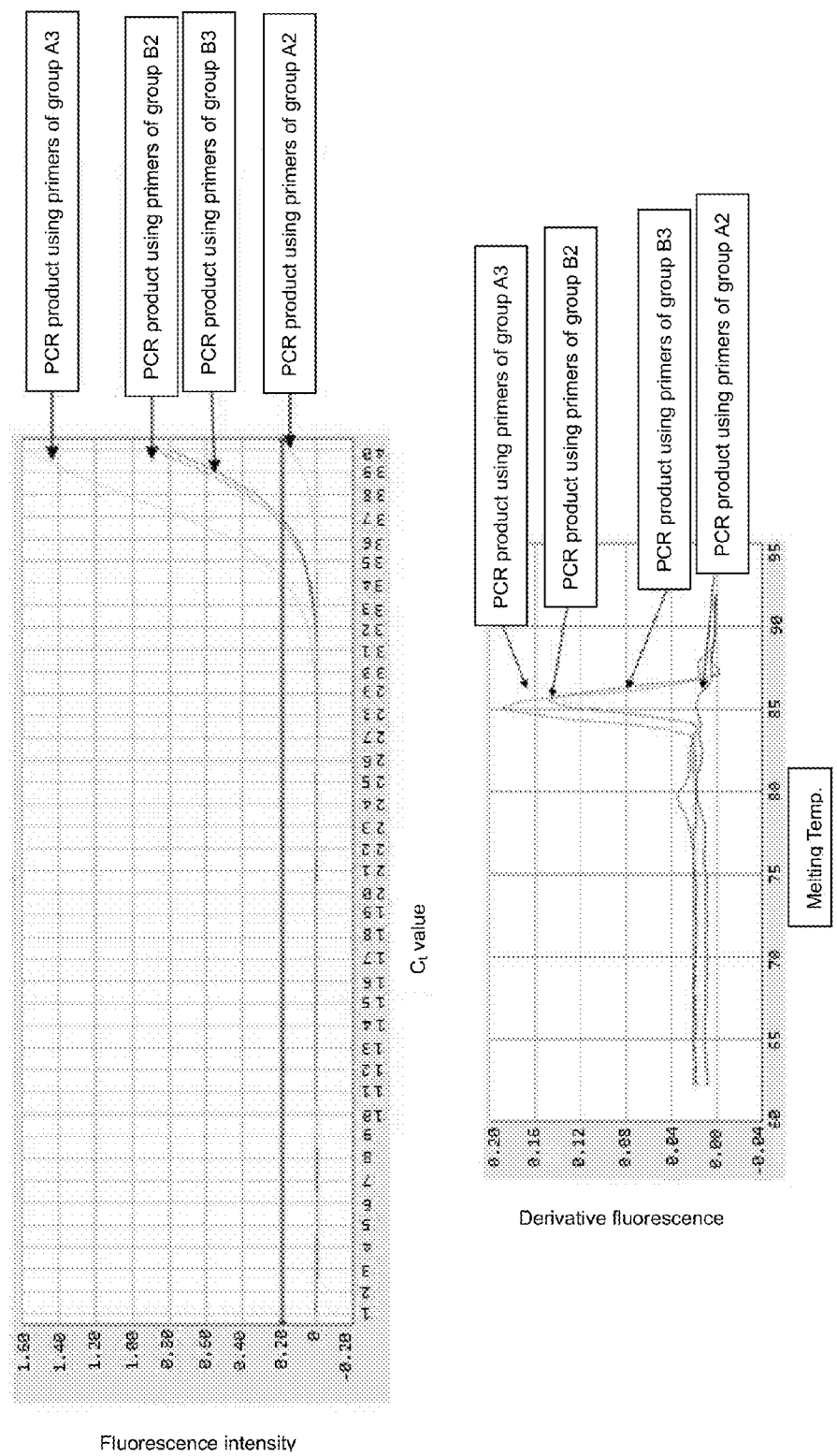

5. Assessment on the Real-Time AS-PCR
  5.1 Tests on the Positive Control Plasmids
  Three pBluescript II(SK(+) plasmids containing the genome DNA fragments of SAA1 alleles (α, β, γ) were used as the positive controls for the real-time AS-PCR, i.e., human SAA1α allele plasmid, human SAA1β allele plasmid, human SAA1γ allele plasmid. The real-time AS-PCR system including the primers and the reaction conditions was assessed by testing on the positive controls following further optimization of reaction condition. Finally, the feasibility of the real-time AS-PCR in the clinical setting was evaluated.
  For example, when SAA1β allele plasmid was used as a template, the reaction conditions were: 95° C. for 5 minutes; 60° C. for 20 seconds; 72° C. for 45 seconds; and 36 cycles. Analysis of SAA1 genotype was conducted based on $C_T$ values and melting curve of the PCR.
  In this Example, four groups of the primers (a pair of the common forward primer and the reverse primer of groups A3, B3, A2 and B2, respectively) were used in the PCR. The amplification results are shown in FIG. 2.
  Results in FIG. 2A showed that the melting curve of the amplified products were consistent with only one peak, which means the primers of the four groups had a good specificity; and there were no signals indicating primer dimers or other non-specific products.
  Results from FIG. 2B and FIG. 2C showed that PCR reaction using the primers of group A3 (labeled as B1 in FIG. 2C) generated an amplified product (CT value of 26.63); using the primers of group B2 (labeled as B4 in FIG. 2C) (CT value of 23.93), whereas the PCR reaction using the primers of group A2 (labeled as B3 in FIG. 2C) and group B3 (labeled as B2 in FIG. 2C) did not generate amplified products. The results confirmed that DNA template in the reaction system was SAA1β type plasmid, which was consistent to the prediction as shown in Table 7. In summary, the real-time AS-PCR result of SAA1β/β genotype was: there were amplified products when using the primers of groups A3 and B2 whereas there were no amplified products when using primers of groups B3 and A2.
  Experiments were also conducted on other five genotypes (α/α, γ/γ, α/β, α/γ and γ/β) using mixed plasmids accordingly as templates, and the results showed consistency to the prediction as shown in Table 7. Therefore, the real-time AS-PCR of the present invention can be used for the SAA1 genotyping.
  5.2 Test on Human Genome DNA Sample
  Test result of a sample with known SAA1 genotype (α/β genotype) is shown in FIG. 3A, wherein the melting curve of the amplified product and the fluorescence amplification curve of PCR products indicated the number of cycles, $C_T$ values of the PCR products using the primers of the groups A3, B3, A2 and B2, which showed all positive amplifications and thereby it is the human SAA1α/β genotype that validated the real-time AS-PCR of the present invention worked with human sample.
  Test result of a sample with known SAA1 genotype (β/β genotype) is shown in FIG. 3B, wherein the melting curve of the amplified product and the fluorescence amplification curve of PCR products indicated the number of cycles, $C_T$ values of the PCR products using the primers of the groups A3, B3, A2 and B2, which showed positive amplification for the A3 and B2 groups and negative for the A2 and B3, and thereby it is human SAA1β/β genotype.
  Test result of a sample with known SAA1 genotype (γ/β genotype) is shown in FIG. 3A, wherein the melting curve of the amplified product and the fluorescence amplification curve of PCR products indicated the number of cycles, $C_T$ values of the PCR products using the primers of the groups A3, B3, A2 and B2, which showed positive amplification for the A3, B3 and B2 groups and negative for the A2, and thereby it is human SAA1γ/β genotype.
6. Optimization of the Real-Time AS-PCR
  6.1 Because the presence of non-specific amplification and the primer dimerization are common concerns for PCR, in the present invention, a pfu DNA polymerase that has the 5' to 3'terminus synthetase activity and 3' to 5' terminus DNA exonuclease activity was used, thereby DNA can be synthesized and meanwhile the mismatched nucleotides can also be promptly excised, which greatly improved specificity of PCR, and in the meantime lowered generation of primer dimers.
  6.2 Modifying the end of primer 3' terminus by thiophosphorylation, so as to prevent the end nucleotide of the primer from degradation by the 3' to 5' terminal DNA exonuclease of pfu DNA polymerase when mismatch occurred, and thereby further prevent from non-specific amplification.
  6.3 Optimizing and selecting the preferred reaction conditions such as concentration of primer (0.5-5 mM), primer length (20-30 bp), annealing temperature (60° C.-67° C.), amplified product length (120-200 bp), template genome DNA concentration (5-15 ng), amplification condition and so on, so as to further improve the efficiency and specificity of the real-time AS-PCR of the present invention.

II. Experimental Results
1. Results of this example, i.e., the distributions of SAA1 genotypes in hepatitis B patients and HBV related liver cirrhosis patients, are shown in Table 8. Among 103 cases of the HBV related liver cirrhosis patients, 92 cases were SAA1β/β homozygote, which had the highest percentage of 89.32%. Among 427 cases of healthy controls, 37 cases were SAA1β/β homozygote with a percentage of 8.67%. It was shown from the comparison that the percentage of SAA1β/β homozygote in the HBV related liver cirrhosis patients was 10.3 times that in the healthy controls (8.67%). The percentage of SAA1β/β homozygote in hepatitis B patients was 31.82%, which was 3.67 times that in the healthy controls (8.67%). A strong correlation between the SAA1β/β homozygote and the HBV related liver cirrhosis was observed, which implied that the SAA1β/β homozygote could be used as a biomarker of HBV related liver cirrhosis.

TABLE 8

Distribution of SAA1 genotypes in healthy controls, hepatitis B patients, and liver cirrhosis patients

| SAA1 genotype | Healthy control | Hepatitis B (HBV) | Hepatitis B liver cirrhosis | Other liver cirrhosis* |
|---|---|---|---|---|
| | | Cases of patients (%) | | |
| β/β | 37(8.67) | 21(31.82) | 92(89.32) | 4(33.33) |
| α/β | 176(41.22) | 18(27.27) | 3(2.91) | 3(25.00) |
| β/γ | 148(34.67) | 24(36.36) | 7(6.8) | 4(33.33) |
| α/γ | 40(9.37) | 0(0) | 0(0) | 0(0.00) |
| α/α | 9(2.11) | 1(1.52) | 1(0.97) | 0(0.00) |
| γ/γ | 17(3.98) | 2(3.03) | 0(0.00) | 1(8.33) |
| Total | 427(100.00) | 66(100.00) | 103(100.00) | 12(100.00) |

*other liver cirrhosis: 3 patients of primary biliary cirrhosis, 9 patients of schistosomiasis cirrhosis.

Considering that the extremely high frequency of SAA1β/β homozygote (89.32%) in the HBV related liver cirrhosis has reached 89.32%, the present invention analyzed and evaluated the use of SAA1β/β homozygote as a risk factor of hepatitis B developing to liver cirrhosis.

Figure 4:
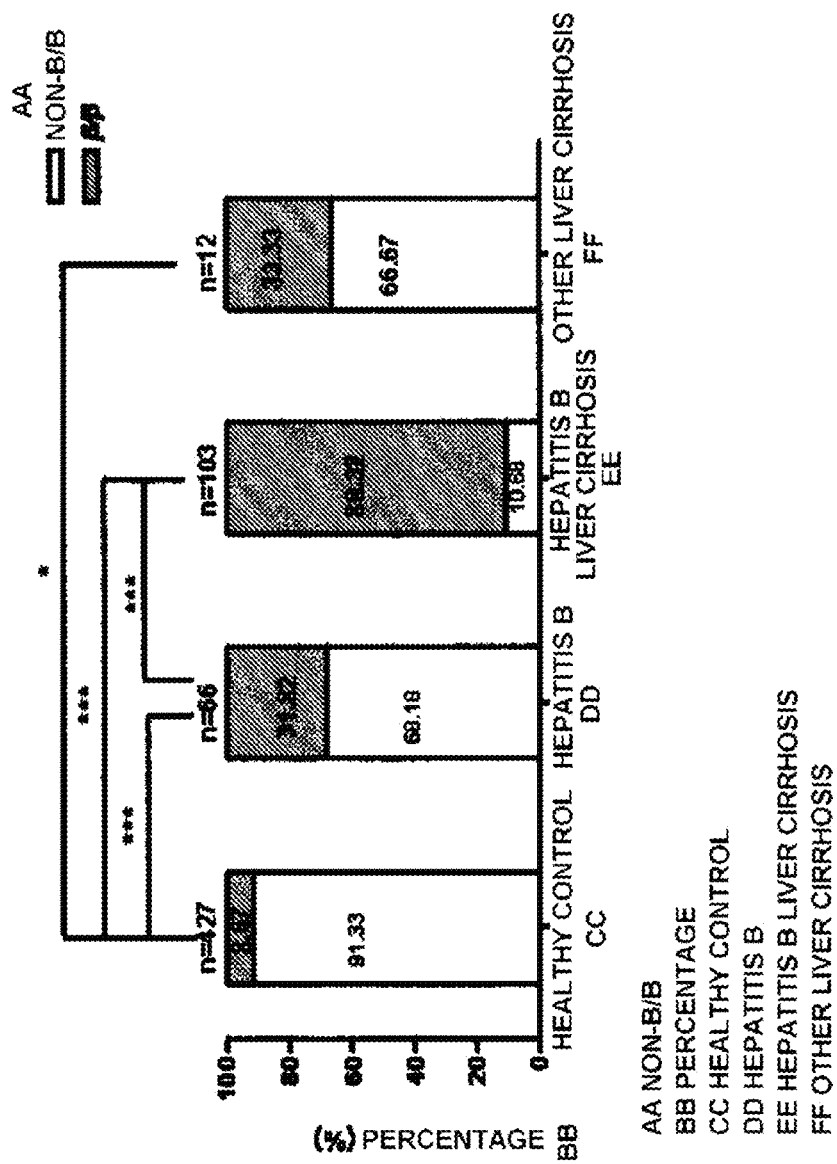
FIG. 4: the percentage histogram of the SAA1β/β and the SAA1 non-β/β types in healthy controls, hepatitis B patients, HBV related liver cirrhosis patients and non-HBV related liver cirrhosis patients.

Percentages of SAA1β/β homozygote and non-SAA1β/β homozygote in the healthy controls, the hepatitis B patients, the HBV related liver cirrhosis, and the HBV irrelated liver cirrhosis were shown in FIG. 4 and Table 8. The percentage of SAA1β/β homozygote was only 8.67% in the healthy controls (n=427), whereas 89.32% in the HBV related liver cirrhosis (n=103), which was about 10 times of that in the healthy controls; in addition, the percentage was 33.33% in the non-HBV irrelated liver cirrhosis patients, which was 2.67 times lower than that in the HBV related liver cirrhosis patients; meanwhile the percentage was 31.82% in the hepatitis B patients (n=66), which was 3 times of that in the healthy controls. The above results indicated that SAA1β/β homozygote was highly correlated to the HBV related liver cirrhosis, and therefore can be used for the diagnosis of the HBV related liver cirrhosis and for the screening of susceptible hepatitis B patients to liver cirrhosis.

Example 3

Correlation Between the SAA1β/β Homozygote and the Hepatitis B Viral Load

Studies have reported that chronic hepatitis B patients who have been experiencing active virus replication in vivo, i.e., HBV DNA reached >$10^5$-$10^6$ copies/mL or hepatitis e antigen (HBeAg) been detected in the blood serum with PCR method, have a highly increased risk of developing to liver cirrhosis. We therefor, measured the hepatitis B viral load in hepatitis B patients having the SAA1β/β homozygote, and the correlation between SAA1β/β homozygote and hepatitis B viral load was analyzed.

I. Method

1. Serum of the hepatitis B patients was collected, and the HBV viral load was assessed based on the amount of HBV DNA in the serum using an HBV nucleotide quantitative detection kit (care HBV PCR assay, QIAGEN). The detection was followed by the instruction of the manufactory, with LightCycler 480 (Roche, Switzerland). The detectable range of the method was $5 \times 10^2$ to $5 \times 10^7$ copies/mL.

2. Results were analyzed so as to study the correlation between the HBV load and the SAA1β/β homozygote.

II. Analysis of the Correlation Between the SAA1β/β Homozygote and the HBV Load

The hepatitis B patients were grouped into two groups of the SAA1β/β homozygote and the non-SAA1β/β homozygote and their HBV DNA contents were compared. Significant difference between the two groups was analyzed by using two-tailed student t-Test.

Figure 5:
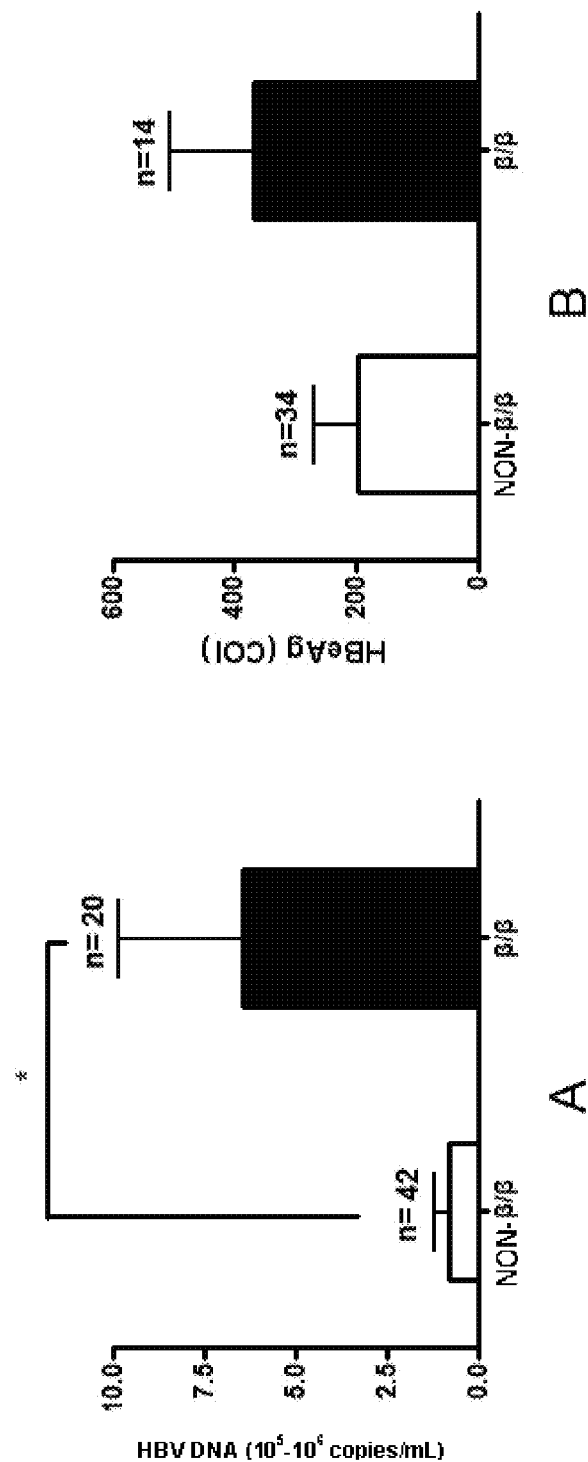
FIG. 5: the significant difference of HBV DNA amounts between the SAA1β/β homozygote and the non-SAA1β/β homozygote hepatitis B. patients.

Results are shown in FIG. 5. In the hepatitis B patients, the HBV DNA content in the SAA1β/β homozygote group (n=20) was significantly higher than that in the non-SAA1β/β homozygote group (n=42) with a P value of 0.02, which suggested the SAA1β/β homozygote was positively correlated to the load of HBV in hepatitis B patients load.

Difference in the load of HBV between the SAA1β/β homozygote and the non-SAA1β/β homozygote indicated that Hepatitis B patients with the SAA1β/β homozygote might have lower capability of virus clearance that results in a constant viral invasion into liver leading into chronic inflammation, causing necrosis of liver cells and finally progressed into liver cirrhosis.

Taken together, present invention has disclosed that the hepatitis B patients with SAA1β/β homozygote had a more active virus replication in vivo and was vulnerable to developing into liver cirrhosis, as compared with the hepatitis patients with the non-SAA1β/β homozygote. Therefore the SAA1β/β homozygote can be used as a risk factor of liver cirrhosis in the prognosis of liver cirrhosis in hepatitis patients.

Example 4

Use of SAA1β/β Homozygote as a Risk Factor of Liver Cirrhosis in the Prognosis and Diagnosis of Liver Cirrhosis The SAA1β/β homozygote as a risk factor of liver cirrhosis applying in the prognosis and diagnosis of liver cirrhosis was evaluated based on the analyses of the distributions of SAA1 genotypes in the healthy controls, the hepatitis B patients and the HBV related liver cirrhosis patients.

Analysis Method and Result:

Logistic regression analysis was conducted with SPSS software to define whether the SAA1β/β homozygote is an independent risk factor in the development from hepatitis B to HBV related liver cirrhosis. It can be seen from the results that, among all other liver cirrhosis related experimental criteria tested in present invention, odds ratio (OR) of the SAA1β/β homozygote was 17.92 (P<0.001), which was the highest. The results support that the SAA1β/β homozygote is an independent risk factor of HBV related liver cirrhosis, that is, hepatitis B patients with the SAA1β/β homozygote genotype have the highest risk developing to liver cirrhosis.

Analysis on the prognosis value of development from hepatitis B to liver cirrhosis has found that the area under ROC (Receiver Operating Characteristic) curve of the SAA1β/β homozygote reached 0.790 (P<0.001), which revealed a very high prognosis value of hepatitis B to liver cirrhosis.

The analyses with ROC curve and univariate logistic regression of the SAA1β/β homozygote in prognosis and diagnosis of HBV related liver cirrhosis demonstrated that the SAA1β/β homozygote was a high-risk factor of hepatitis B developing to liver cirrhosis. Furthermore, in the comparison with other risk factors (see Table 9), the SAA1β/β homozygote provided the highest diagnostic value in the prognosis of hepatitis B patients (AUC=0.790, p<0.001).

TABLE 9 the SAA1 β/β homozygote is a high-risk factor of hepatitis B developing to liver cirrhosis.
Logistic regression analysis of independent risk factors

| parameters | n | OR | ρ | 95% CI low | 95% CI high |
|---|---|---|---|---|---|
| β/β | 169 | 17.922 | 0.000 | 7.957 | 40.366 |
| AST/ALT | 159 | 4.301 | 0.000 | 2.005 | 9.225 |
| CRP | 91 | 1.112 | 0.012 | 1.024 | 1.204 |
| TBA | 167 | 1.014 | 0.005 | 1.004 | 1.024 |
| Lp (a) | 171 | 0.990 | 0.008 | 0.982 | 0.997 |
| LDL | 111 | 0.544 | 0.027 | 0.317 | 0.933 |
| HDL | 111 | 0.340 | 0.028 | 0.130 | 0.890 |
| ApoA1 | 111 | 0.124 | 0.002 | 0.033 | 0.457 |
| ALT | 167 | 0.994 | 0.034 | 0.989 | 1.00 |

Example 5

Use of the SAA1β/β Homozygote as a Biomarker of Liver Cirrhosis in the Diagnosis of Liver Cirrhosis Biomarker is a biochemical indicator, which is an abnormal signal at the molecular level, or the cell level or the organism level by a biological organism before suffering from severe damage, which can be used in the detection and assessment of the physiology, pathology, or changes under medical treatment. It is of medical significance in the early diagnosis, the prevention and treatment by monitoring the changes of the biomarkers.

It can be seen from the previous four examples that, the SAA1β/β homozygote possessed a very high proportion (89.32%) in the HBV related liver cirrhosis. Furthermore, the hepatitis B virus load in the hepatitis patients with the SAA1β/β homozygote was significantly higher than that in patients with the non-SAA1β/β homozygote, which suggested during the development from hepatitis B to hepatitis B liver cirrhosis, hepatitis patients with the SAA1β/β homozygote might have lower capability of virus clearance resulting in a persistence of the HBV infection leading into chronic inflammation of liver cells causing necrosis of liver cells and the proliferation of fibroblast cells in liver, and finally progressing into liver cirrhosis. In order to assess the SAA1β/β homozygote as a risk factor of liver cirrhosis in prognosis of the disease, the univarate logistic regression analysis was performed, which demonstrated that the SAA1β/β homozygote was a high-risk factor of hepatitis B developing to liver cirrhosis, with the OR value as 17.92 (P<0.001). Taken together, the SAA1β/β homozygote is well correlated with the development of hepatitis B to liver cirrhosis, and can be used as a biomarker of HBV related liver cirrhosis. It can be applied in the prognosis and the early diagnosis of the disease to achieve prevention of disease.

OR values of various criteria in the HBV related liver cirrhosis were analyzed using regression analysis, and results are shown in Table 10. Besides the SAA1β/β homozygote, AST/LTL, SAA1, TBA and LDL showed certain value in the diagnosis of HBV related liver cirrhosis. Among them, OR value of the SAA1β/β homozygote was particularly high, SAA1β/β with OR value reached 1508.152 (95% confident interval: 20.855~109061.936) analyzed with a fitting formula.

Figure 7:
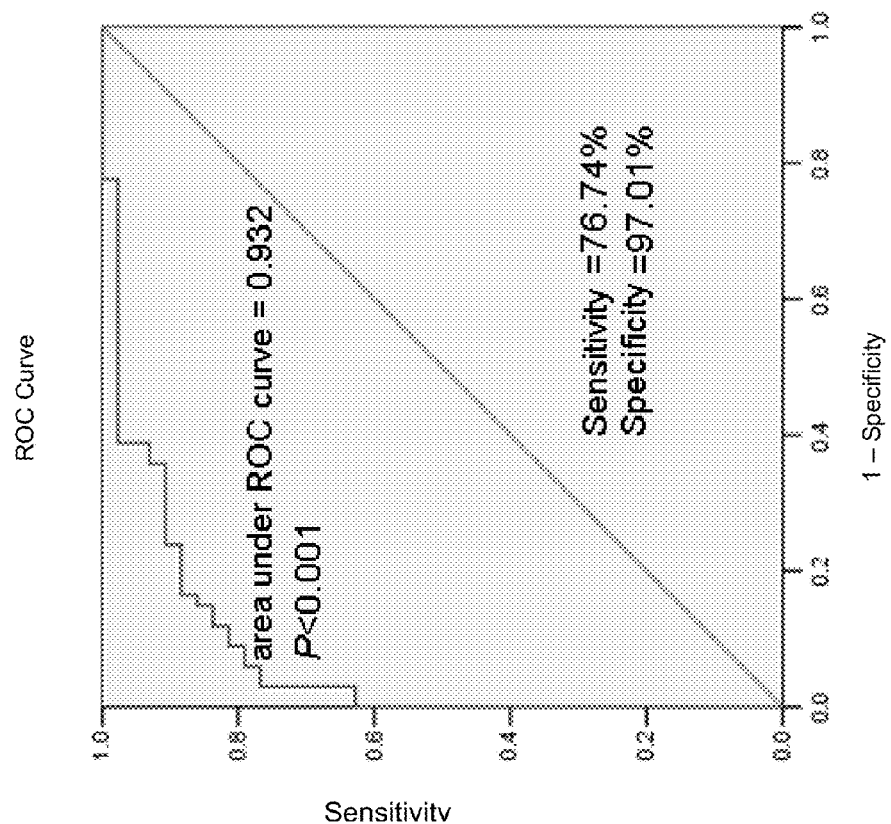
FIG. 7: the ROC curve of the combining use of SAA1β/β homozygote, AST/ALT, TBA, and LDL in the diagnosis of liver cirrhosis.

By further logistic regression analysis in association with the ROC curve analysis, a combination of the multiple factors (the SAA1β/β homozygote, AST/LTL ratio, SAA1, TBA, and LDL) could enhance the non-invasive diagnostic value in the HBV related cirrhosis with the area under ROC curve reaching 0.932(P<0.001) with 97.01% specificity and 76.74% sensitivity (FIG. 7). In summary, these criteria can be used in the non-invasive diagnosis of the HBV related liver cirrhosis. The formula for determination value is:

$$P=1/(1+e^{-(-14.08+1.94AST/ALT+0.026TBA+7.32SAA1\ geno\_type-1.29LDL)}),$$

wherein the cutoff value is 0.66.

That is, when a value calculated based on the above formula equals to or is greater than 0.66, a patient might have a possibility of suffering from liver cirrhosis.

Figure 6:
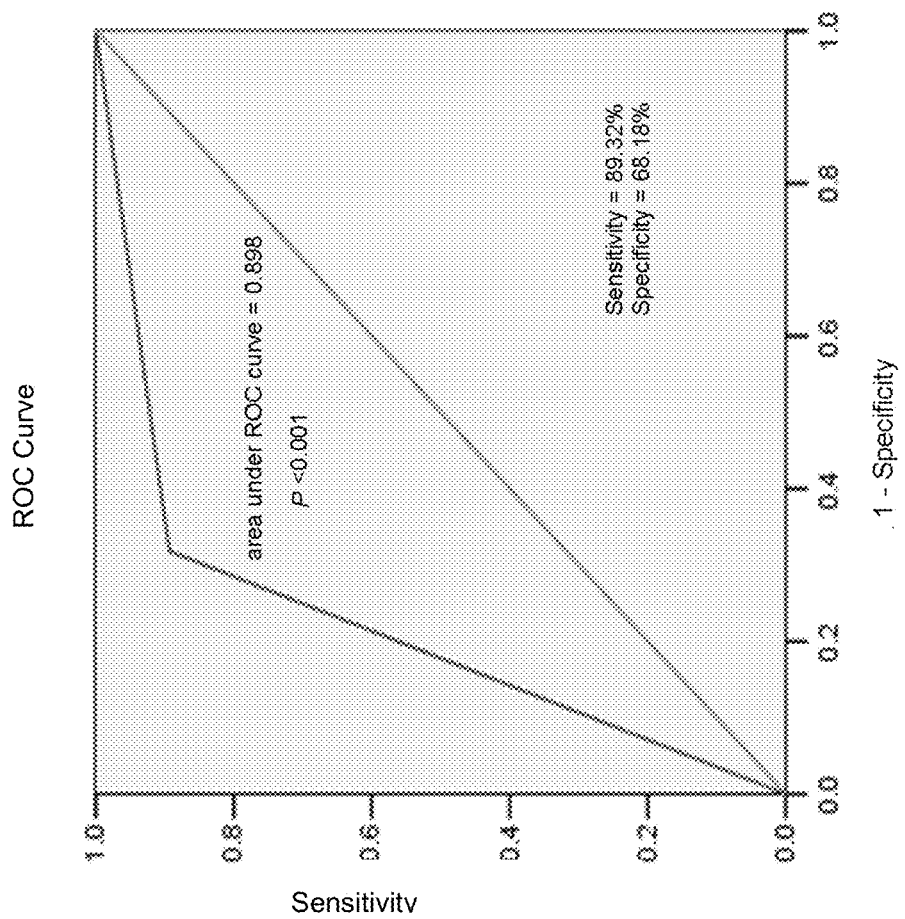
FIG. 6: the ROC curve of SAA1β/β homozygote in the prognosis and diagnosis of liver cirrhosis.

In summary, the distribution of the SAA1β/β homozygote in Chinese Han population is obviously different from that in Caucasian and Japanese. The frequency of allele β in Chinese is the highest as 46.6%, which is 2.47 times that of Caucasian (18.9%), and is also higher than that of Japanese (30.1%). And allele β is highly correlated to the concentration of SAA1 protein (r=0.135, p=0.005, datas not shown). The percentage of the SAA1β/β homozygote in the HBV related liver cirrhosis patients (89.32%) is greatly higher than that in the healthy controls (8.67%). The SAA1β/β homozygote is also predominant in the hepatitis B patients, which is 3.67 times that in the healthy controls, and is intermediate between that in the liver cirrhosis patients and that in the healthy controls. Secondly, the ROC curve of the SAA1β/β homozygote and the logistic regression analysis in the prognosis of the HBV related liver cirrhosis have demonstrated that the SAA1β/β homozygote is a high risk factor of hepatitis B developing to liver cirrhosis with the OR value as 17.92 (p<0.001). This result suggested very significant correlation between the SAA1β/β homozygote and HBV related liver cirrhosis. Moreover, the SAA1β/β homozygote has a high diagnostic value in the prognosis of the liver cirrhosis and early diagnosis of the hepatitis B patients (as shown in FIG. 6, AUC=0.898, p<0.001). In the early non-invasive diagnosis of the HBV related liver cirrhosis in combination with other criteria such as AST/LTL ratio, SAA1, TBA, and LDL, the area under ROC curve can reach 0.932 (p<0.001) with 97.01% specificity and 76.74% sensitivity. When a value calculated based on the above formula equals to or is greater than 0.66, the hepatitis B patient is very likely to have developed to liver cirrhosis with 97.01% specificity and 76.74% sensitivity.

The present invention disclosed that the SAA1β/β homozygote as a liver cirrhosis biomarker can be used as a risk factor of HBV related liver cirrhosis in the prognosis and diagnosis of liver cirrhosis; the SAA1β/β homozygote is applicable for screening the susceptible or high-risk population of liver cirrhosis in the hepatitis B patients, and thereby achieving early diagnosis, early prevention, and early intervention, so as to greatly lower the incidence of liver cirrhosis, liver cancer and improve the life quality of the patients.

TABLE 10

Logistic regression analysis of risk factors

| | | | | 95% CI | |
| --- | --- | --- | --- | --- | --- |
| Item | n | OR | p | Low | High |
| β/β | 169 | 1508.152 | 0.001 | 20.855 | 109061.936 |
| AST/ALT | 159 | 6.922 | 0.012 | 1.517 | 31.585 |
| SAA1 | 170 | 1.190 | 0.017 | 1.032 | 1.372 |
| TBA | 167 | 1.026 | 0.005 | 1.008 | 1.045 |
| LDL | 111 | 0.275 | 0.013 | 0.099 | 0.762 |

Analysis on diagnosis value of ROC curve

| | | | | 95% CI | |
| --- | --- | --- | --- | --- | --- |
| Item | n | AUC | p | Low | High |
| β/β | 169 | 0.898 | <0.001 | | |
| AST/ALT | 159 | 0.712 | <0.001 | 0.630 | 0.794 |
| TBA | 167 | 0.779 | <0.001 | 0.705 | 0.853 |
| LDL | 111 | 0.689 | <0.001 | 0.584 | 0.795 |
| combine parameters listed above | 111 | 0.932 | <0.001 | 0.883 | 0.982 |

Example 6

This Example provided a real-time allele-specific PCR test kit for detecting the SAA1 allele SNP with genomic.

The kit can detect SAA1α, β, γ alleles in human genomes, and is suitable for the classification of human SAA1 genotypes.

Components of the kit comprise the followings.

| Category | reagent | specification |
|---|---|---|
| Sample-treating reagents | Genomic DNA dilutent | 5 mL |
| PCR reagent Real-time PCR instrument: THERMAL CYCLER DICE ® REAL TIME SYSTEM; SMART CYCLER ® SYSTEM/SMART CYCLER ® II SYSTEM (CEPHEID); APPLIED BIOSYSTEMS 7900HT/7300/7500 REAL-TIME PCR SYSTEM, 7500 FAST REAL-TIME PCR SYSTEM, STEPONEPLUS ™ REAL-TIME PCR SYSTEM (AppliedBiosystems); LightCycler ® (Roche Diagnostics); MX3000P ™ (Stratagene) | PCR reagent A | 1 mL × 1 |
| | PCR reagent B | 1 mL × 1 |
| | PCR reagent C | 1 mL × 1 |
| | PCR reagent D | 1 mL × 1 |
| | PCR reagent E | 50 μL × 1 |
| | PCR reagent F | 50 μL × 1 |
| | PCR reaction liquid G | 0.5 mL × 1 |
| Control reagents | Negative control | 1 mL × 1 |
| | Positive control 1 | 1 mL × 1 |
| | Positive control 2 | 1 mL × 1 |
| | Positive control 3 | 1 mL × 1 |

PCR reagent A: 10×PCR buffer solution+the primers of group A3

PCR reagent B: 10×PCR buffer solution+the primers of group B3

PCR reagent C: 10×PCR buffer solution+the primers of group A2

PCR reagent D: 10×PCR buffer solution+the primers of group B3

PCR reagent E: 20×SYBR GREEN (cyanine-containing dye) I fluorescent dye

PCR reagent F: 20×ROX (fluorescent dye) fluorescence calibration solution

PCR reagent G: pfu DNA polymerase

Positive control 1: plasmid containing genomic NDA fragment of human SAA1a allele Positive control 2: plasmid containing genomic NDA fragment of human SAA1b allele Positive control 3: plasmid containing genomic NDA fragment of human SAA1g allele Transportation and storage conditions for the reagents: The present kit can be transported at a temperature of 2~8° C., and stored at a temperature of −20° C.

Expiration date: The present kit will be expired in 12 months after production, and should be used before expiration.

The Procedure is as Follows:

1. Preparing human genomic DNA sample to final concentration at 10 ng/μL;
2. Adding 2 μL of the prepared sample into four PCR reaction tubes, respectively,
3. Adding 10 μL PCR reagent A, B, C and D into the above four PCR reaction tubes, respectively;
4. Adding 1 μL PCR reagent E into the above four PCR reaction tubes, respectively;
5. Adding 1 μL PCR reagent F into the above four PCR reaction tubes, respectively;
6. Adding 8 μL PCR reagent G into the above four PCR reaction tubes, respectively;
7. Treating the negative control, positive control 1, 2, and 3 in accordance with the above methods,
8. Mixing the above prepared reaction solution and centrifuging at 5000 rpm for 3 minutes;
9. Setting the prepared reaction tubes into a real-time PCR instrument for amplification;
10 Setting the reaction cycles: 95° C. for 10 minutes; 95° C. for 30 seconds; 62° C. for 31 seconds; 72° C. for 45 seconds; 35 cycles.

SAA1 genotypes of 427 cases of the healthy Chinese Han population and 103 cases of liver cirrhosis patients were determined with the present kit. The results were shown in the examples as listed above. It can be seen that the kit of the present invention can be used not only for the study of the SAA1 genotype distribution in the healthy population, but also for the study of correlations between SAA1 genotypes and various diseases. As shown in the above examples, the percentage of the SAA1β/β homozygote was much higher in liver cirrhosis patients than in healthy controls, therein the SAA1β/β homozygote was a risk factor of liver cirrhosis. In summary, the present kit is applicable for screening the susceptible or high-risk population of liver cirrhosis in the hepatitis B patients, to achieve early diagnosis, early prevention, and early intervention, which could dramatically reduce the incidence of liver cirrhosis and liver cancer, and thereby improves the life quality of patients.

What is claimed:

1. A method of diagnosing liver cirrhosis and/or determining the prognosis of hepatitis B associated liver cirrhosis which comprises identifying the presence of SAA1 β/β homozygote with real-time allele-specific PCR;
which comprises
constructing synthetic primers according to the gene sequences of three SAA1α, β and γ alleles,
amplifying samples to be tested by real-time allele-specific PCR, and
determining the genotypes of the PCR-amplified products based on CT value and melting curve;
wherein the primers comprise:

```
1) A pair of primers of group A3:
Forward primer 5'-3' sequence (SEQ ID NO: 1):
TCCCTTCTGCCTTTCCTTTCCTTTCC, Reverse primer 5'-3' sequence (SEQ ID NO: 2):
TTACGTGATCGCTTCTGCAGCCCAGG;

2) A pair of primers of group A2:
Forward primer 5'-3' sequence (SEQ ID NO: 1):
TCCCTTCTGCCTTTCCTTTCCTTTCC, Reverse primer 5'-3' sequence (SEQ ID NO: 3):
TTACGTGATCGCTTCTGCAGCCCAGA;

3) A pair of primers of group B3:
Forward primer 5'-3' sequence (SEQ ID NO: 1):
TCCCTTCTGCCTTTCCTTTCCTTTCC, Reverse primer 5'-3' sequence (SEQ ID NO: 4):
TCCCAGGAGCTCCAGTTACGTGATCG;

4) A pair of primers of group B2:
Forward primer 5'-3' sequence (SEQ ID NO: 1):
TCCCTTCTGCCTTTCCTTTCCTTTCC, Reverse primer 5'-3' sequence (SEQ ID NO: 5):
TCCCAGGAGCTCCAGTTACGTGATCA.
```

2. The method of claim 1, wherein the primers have a 3' terminus end, which is modified by thiophosphorylation.

3. The method of claim 1, wherein a reaction system of real-time allele-specific PCR comprises,

```
1) A pair of primers of group A3:
Forward primer 5'-3' sequence (SEQ ID NO: 1):
TCCCTTCTGCCTTTCCTTTCCTTTCC, Reverse primer 5'-3' sequence (SEQ ID NO: 2):
TTACGTGATCGCTTCTGCAGCCCAGG;

2) A pair of primers of group A2:
Forward primer 5'-3' sequence (SEQ ID NO: 1):
TCCCTTCTGCCTTTCCTTTCCTTTCC, Reverse primer 5'-3' sequence (SEQ ID NO: 3):
TTACGTGATCGCTTCTGCAGCCCAGA;

3) A pair of primers of group B3:
Forward primer 5'-3' sequence (SEQ ID NO: 1):
TCCCTTCTGCCTTTCCTTTCCTTTCC, Reverse primer 5'-3' sequence (SEQ ID NO: 4):
TCCCAGGAGCTCCAGTTACGTGATCG;

4) A pair of primers of group B2:
Forward primer 5'-3' sequence (SEQ ID NO: 1):
TCCCTTCTGCCTTTCCTTTCCTTTCC, Reverse primer 5'-3' sequence (SEQ ID NO: 5):
TCCCAGGAGCTCCAGTTACGTGATCA,
``` a genomic DNA of human SAA1α, β, γ alleles to be tested, a pfu DNA polymerase, a reaction buffer and a fluorescent dye.

4. The method of claim 1, wherein in the real-time allele-specific PCR, plasmids containing a cloned genomic DNA fragment of the SAA1α, β, γ alleles respectively are used as positive controls, and an empty plasmid is used as a negative control.

5. The method of claim 1, wherein the SAA1 β/β homozygote is used as a risk factor in the prognosis of liver cirrhosis.

6. The method claim 1, wherein the SAA1 β/β homozygote is used as a liver cirrhosis biomarker in the diagnosis of liver cirrhosis.

7. The method of claim 1, wherein the liver cirrhosis is hepatitis B associated liver cirrhosis.

8. A method of identifying liver cirrhosis susceptible populations by SAA1 genotyping, comprising the steps of
constructing synthetic primers according to the gene sequences of three SAA1α, β and γ alleles,
amplifying samples to be tested by real-time allele-specific PCR, and
determining the genotypes of the PCR-amplified products based on CT value and melting curve;
wherein the primers comprise:

```
1) A pair of primers of group A3:
Forward primer 5'-3' sequence (SEQ ID NO: 1):
TCCCTTCTGCCTTTCCTTTCCTTTCC, Reverse primer 5'-3' sequence (SEQ ID NO: 2):
TTACGTGATCGCTTCTGCAGCCCAGG;
```

-continued

```
2) A pair of primers of group A2:
Forward primer 5'-3' sequence (SEQ ID NO: 1):
TCCCTTCTGCCTTTCCTTTCCTTTCC, Reverse primer 5'-3' sequence (SEQ ID NO: 3):
TTACGTGATCGCTTCTGCAGCCCAGA;

3) A pair of primers of group B3:
Forward primer 5'-3' sequence (SEQ ID NO: 1):
TCCCTTCTGCCTTTCCTTTCCTTTCC, Reverse primer 5'-3' sequence (SEQ ID NO: 4):
TCCCAGGAGCTCCAGTTACGTGATCG;

4) A pair of primers of group B2:
Forward primer 5'-3' sequence (SEQ ID NO: 1):
TCCCTTCTGCCTTTCCTTTCCTTTCC, Reverse primer 5'-3' sequence (SEQ ID NO: 5):
TCCCAGGAGCTCCAGTTACGTGATCA.
```

9. The method of claim 8, wherein the primers further comprise extension fragments of primers SEQ ID NO:1-SEQ ID NO:5.

10. The method of claim 8, wherein the primers have a 3' terminus end, which is modified by thiophosphorylation.

11. The method of claim 8, wherein the conditions of the real-time allele-specific PCR are optimized with the annealing temperature being 60-67° C., the amplified product length being 120-200 bp, and the concentration range of genome DNA to be tested being 5-15 ng.

\* \* \* \* \*

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Synthetic

<400> SEQUENCE: 1
tcccttctgc ctttcctttc ctttcc          26

```
<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
ttacgtgatc gcttctgcag cccagg                                          26

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
ttacgtgatc gcttctgcag cccaga                                          26

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
tcccaggagc tccagttacg tgatcg                                          26

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
tcccaggagc tccagttacg tgatca                                          26

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
catggtatcc aaggctgcta tgat                                            24

<210> SEQ ID NO 7
<211> LENGTH: 26
<212> TYPE: DNA
<213> ORGANISM: Artificial Sequence
<220> FEATURE:
<223> OTHER INFORMATION: Synthetic

<400> SEQUENCE: 7
atgaggaatc actcactcct accatc                                          26

<210> SEQ ID NO 8
<211> LENGTH: 461
<212> TYPE: DNA
<213> ORGANISM: Homo sapiens

<400> SEQUENCE: 8
```

-continued

```
atggtatcca aggctgctat gatcacaggc tgaaagcttg aagtcagtgg aagatttgtc      60
cttcctcatt cccctctaag gtgttgttgg agtctttatg ttctcctgat gtcccttctg     120
cctttccttt cctttccagg ggctcgggac atgtggagag cctactctga catgagagaa     180
gccaattaca tcggctcaga caaatacttc catgctcggg ggaactatga tgctgccaaa     240
aggggacctg ggggtgcctg ggctgcagaa gtgatcacgt aactggagct cctgggacgt     300
tagggctggg tgagcagagc ttgcctgcct tggacagtca ggagggagac gagctccttg     360
tggagaagtt agaggctgcg gcccctcctc ctcttgccct ctctctgcct ctgtgctcag     420
tgtgaggtct gagtggatgg taggagtgag tgattcctca t                         461
```